United States Patent
Wersland et al.

(10) Patent No.: US 11,957,635 B2
(45) Date of Patent: *Apr. 16, 2024

(54) PERCUSSIVE THERAPY DEVICE WITH VARIABLE AMPLITUDE

(71) Applicant: Therabody, Inc., Los Angeles, CA (US)

(72) Inventors: Jason Wersland, Manhattan Beach, CA (US); Benjamin Nazarian, Los Angeles, CA (US); Jaime Sanchez Solana, Los Angeles, CA (US); Eduardo Merino, Los Angeles, CA (US); Richard Tang, Shenzhen (CN)

(73) Assignee: Therabody, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/515,158

(22) Filed: Oct. 29, 2021

(65) Prior Publication Data

US 2022/0047453 A1 Feb. 17, 2022

Related U.S. Application Data

(63) Continuation of application No. 17/018,044, filed on Sep. 11, 2020, now Pat. No. 11,160,721, which is a
(Continued)

(51) Int. Cl.
*A61H 23/00* (2006.01)
*A61H 1/00* (2006.01)
(Continued)

(52) U.S. Cl.
CPC ........... *A61H 23/006* (2013.01); *A61H 1/008* (2013.01); *A61H 15/0085* (2013.01);
(Continued)

(58) Field of Classification Search
CPC .. A61H 23/006; A61H 1/008; A61H 15/0085; A61H 23/00; A61H 23/0254;
(Continued)

(56) References Cited

U.S. PATENT DOCUMENTS

| 657,765 A | 9/1900 | Gibbs |
| 675,772 A | 6/1901 | Ferguson |

(Continued)

FOREIGN PATENT DOCUMENTS

| AT | 510048 A1 | 1/2012 |
| AU | 2019204770 B1 | 10/2019 |

(Continued)

OTHER PUBLICATIONS

TheraGun device in YouTube video "TheraGun: What It Does," https://www.youtube.com/watch?v=FB_JTZnD7vs; Aug. 24, 2016 (upload date).

(Continued)

*Primary Examiner* — Colin W Stuart
*Assistant Examiner* — Matthew R Moon
(74) *Attorney, Agent, or Firm* — Sterne, Kessler, Goldstein & Fox P.L.L.C.

(57) ABSTRACT

A percussive therapy device that includes a housing, an electrical source, a motor positioned in the housing, a switch for activating the motor, a push rod assembly operatively connected to the motor and configured to provide reciprocating motion in response to activation of the motor, and a massage attachment secured to a distal end of the push rod assembly. The reciprocating motion of the push rod assembly has a user-adjustable amplitude.

14 Claims, 16 Drawing Sheets

Related U.S. Application Data continuation-in-part of application No. 16/869,402, filed on May 7, 2020, now Pat. No. 10,857,064, which is a continuation-in-part of application No. 16/675,772, filed on Nov. 6, 2019, now Pat. No. 10,702,448, which is a continuation-in-part of application No. 16/357,984, filed on Mar. 19, 2019, now Pat. No. 10,912,707, said application No. 16/357,984 is a continuation of application No. 15/920,322, filed on Mar. 13, 2018, now Pat. No. 10,357,425, which is a continuation-in-part of application No. 15/458,920, filed on Mar. 14, 2017, now abandoned, which is a continuation-in-part of application No. 15/186,859, filed on Jun. 20, 2016, now abandoned.

(60) Provisional application No. 62/899,098, filed on Sep. 11, 2019, provisional application No. 62/844,424, filed on May 7, 2019, provisional application No. 62/785,151, filed on Dec. 26, 2018, provisional application No. 62/182,525, filed on Jun. 20, 2015.

(51) Int. Cl.
| | | |
|---|---|---|
| *A61H 15/00* | (2006.01) | |
| *A61H 23/02* | (2006.01) | |
| *A61B 17/14* | (2006.01) | |
| *B23D 49/00* | (2006.01) | |
| *B23D 49/10* | (2006.01) | |
| *B23D 51/16* | (2006.01) | |
| *B27B 19/00* | (2006.01) | |
| *B27B 19/02* | (2006.01) | |

(52) U.S. Cl.
CPC ......... *A61H 23/00* (2013.01); *A61H 23/0254* (2013.01); *A61B 17/142* (2016.11); *A61H 2023/029* (2013.01); *A61H 2201/0165* (2013.01); *A61H 2201/12* (2013.01); *A61H 2201/1207* (2013.01); *A61H 2201/1215* (2013.01); *A61H 2201/123* (2013.01); *A61H 2201/14* (2013.01); *A61H 2201/1481* (2013.01); *A61H 2201/149* (2013.01); *A61H 2201/1664* (2013.01); *B23D 49/007* (2013.01); *B23D 49/10* (2013.01); *B23D 51/16* (2013.01); *B27B 19/00* (2013.01); *B27B 19/002* (2013.01); *B27B 19/02* (2013.01)

(58) Field of Classification Search
CPC ...... A61H 2023/029; A61H 2201/0165; A61H 2201/1664; A61H 2201/1481; A61H 2201/149; A61H 2201/12; A61H 2201/1207; A61H 2201/1215; A61H 2201/123; A61H 2201/14; B27B 19/02; B27B 19/00; B27B 19/002; B23D 49/10; B23D 51/16; B23D 49/007; A61B 17/142
USPC ........... 30/392, 393, 183, 189, 277; 81/9.22, 81/465, 57.39; 173/49, 114, 115, 201, 173/205, 29
See application file for complete search history.

(56) References Cited

U.S. PATENT DOCUMENTS

| | | |
|---|---|---|
| 1,545,027 A | 7/1925 | Ashlock |
| 1,594,636 A | 8/1926 | Smith |
| 1,657,765 A | 1/1928 | Pasque |
| 1,784,301 A | 12/1930 | Mekler |
| D91,454 S | 2/1934 | Decker |
| D93,943 S | 11/1934 | Rand |
| 2,179,594 A | 11/1939 | Johnson |
| D118,980 S | 2/1940 | Larson |
| D129,045 S | 8/1941 | Wilhide |
| 2,391,671 A | 12/1945 | Berg |
| D143,678 S | 1/1946 | Snyder et al. |
| 2,475,861 A | 7/1949 | Alfred |
| D161,484 S | 1/1951 | McQuown |
| D163,324 S | 5/1951 | Rittenhouse |
| D180,923 S | 9/1957 | Anton |
| D181,742 S | 12/1957 | Madl |
| 2,931,632 A | 4/1960 | Angelis |
| 2,987,334 A | 6/1961 | Wendling |
| 3,053,559 A | 9/1962 | Norval |
| 3,077,837 A | 2/1963 | Sidney et al. |
| D195,145 S | 4/1963 | Ernest |
| D197,142 S | 12/1963 | Godfrey |
| 3,172,675 A | 3/1965 | Gonzalez |
| D207,505 S | 4/1967 | Whitman |
| 3,452,226 A | 6/1969 | Hettich |
| 3,545,301 A | 12/1970 | Richter |
| 3,626,934 A | 12/1971 | Andis |
| 3,699,952 A | 10/1972 | Waters et al. |
| 3,705,579 A | 12/1972 | Morini et al. |
| D230,522 S | 2/1974 | Rothman |
| D237,454 S | 11/1975 | Adams |
| D237,455 S | 11/1975 | Schramm |
| 3,942,251 A | 3/1976 | Griffies |
| 3,968,789 A | 7/1976 | Simoncini |
| 4,031,763 A * | 6/1977 | Eisenberg ............... B25D 11/12 30/392 |
| 4,046,142 A | 9/1977 | Whitney |
| 4,088,128 A | 5/1978 | Mabuchi |
| 4,150,668 A | 4/1979 | Johnston |
| 4,158,246 A | 6/1979 | Meadows et al. |
| 4,173,217 A | 11/1979 | Johnston |
| 4,203,431 A | 5/1980 | Abura et al. |
| D265,985 S | 8/1982 | House |
| 4,506,159 A | 3/1985 | Reuter et al. |
| 4,513,737 A | 4/1985 | Mabuchi |
| 4,533,796 A | 8/1985 | Engelmore |
| 4,549,535 A | 10/1985 | Wing |
| 4,565,189 A | 1/1986 | Mabuchi |
| 4,566,442 A | 1/1986 | Mabuchi |
| 4,596,406 A | 6/1986 | Van Vleet et al. |
| D287,814 S | 1/1987 | Hiraishi |
| 4,691,693 A | 9/1987 | Sato |
| 4,692,958 A | 9/1987 | McMakin |
| D292,368 S | 10/1987 | Mikiya |
| 4,730,605 A | 3/1988 | Noble et al. |
| D300,132 S | 3/1989 | Culbertson |
| 4,815,224 A | 3/1989 | Miller |
| 4,841,955 A | 6/1989 | Evans et al. |
| D303,373 S | 9/1989 | Ching, Jr. |
| D310,005 S | 8/1990 | Precht |
| D314,320 S | 2/1991 | Brosius |
| 4,989,613 A | 2/1991 | Finkenberg |
| 4,991,298 A | 2/1991 | Matre |
| 5,014,681 A | 5/1991 | Heeman et al. |
| D320,379 S | 10/1991 | Culbertson |
| D321,338 S | 11/1991 | Sakamoto |
| 5,085,207 A | 2/1992 | Fiore |
| 5,088,474 A | 2/1992 | Mabuchi et al. |
| 5,092,317 A | 3/1992 | Zelikovski |
| 5,103,809 A | 4/1992 | DeLuca et al. |
| 5,123,139 A | 6/1992 | Leppert et al. |
| D329,166 S | 9/1992 | Doggett |
| D329,291 S | 9/1992 | Wollman |
| D329,292 S | 9/1992 | Wollman |
| D331,467 S | 12/1992 | Wollman |
| D334,012 S | 3/1993 | Chen |
| 5,201,149 A | 4/1993 | Eisenblatter |
| 5,207,697 A | 5/1993 | Carusillo et al. |
| 5,212,887 A | 5/1993 | Farmerie |
| D338,802 S | 8/1993 | Maass |
| D345,077 S | 3/1994 | Maass |
| D345,727 S | 4/1994 | Flowers |
| D345,888 S | 4/1994 | Joss |
| D349,029 S | 7/1994 | Matsunaga |
| 5,417,644 A | 5/1995 | Lee et al. |
| D363,352 S | 10/1995 | Huen |

(56) References Cited

U.S. PATENT DOCUMENTS

| | | |
|---|---|---|
| D367,712 S | 3/1996 | Young |
| 5,501,657 A | 3/1996 | Feero |
| D374,934 S | 10/1996 | Lie |
| 5,569,168 A | 10/1996 | Hartwig |
| 5,573,500 A | 11/1996 | Katsunuma |
| 5,656,017 A | 8/1997 | Keller et al. |
| 5,656,018 A | 8/1997 | Tseng |
| D383,366 S | 9/1997 | Heck |
| D383,435 S | 9/1997 | Svetlik |
| D384,639 S | 10/1997 | Kawakami |
| D387,728 S | 12/1997 | Kawakami |
| D388,175 S | 12/1997 | Lie |
| D397,991 S | 9/1998 | Kawakami |
| D400,161 S | 10/1998 | Nagele |
| D400,758 S | 11/1998 | Hippen |
| 5,860,669 A | 1/1999 | Wass et al. |
| D408,543 S | 4/1999 | Back |
| 5,910,197 A | 6/1999 | Chaconas |
| 5,925,002 A | 7/1999 | Wollman |
| D412,485 S | 8/1999 | Kato |
| 5,935,089 A | 8/1999 | Shimizu |
| 5,951,501 A | 9/1999 | Griner |
| D417,648 S | 12/1999 | Clowers |
| 6,003,052 A * | 12/1999 | Yamagata ............ G06F 1/1626 345/905 |
| 6,006,631 A | 12/1999 | Miner et al. |
| D425,014 S | 5/2000 | Willkens |
| D430,774 S | 9/2000 | Naft |
| D430,938 S | 9/2000 | Lee |
| D432,077 S | 10/2000 | Zurwelle |
| D433,300 S | 11/2000 | Buck |
| 6,146,383 A | 11/2000 | Studer et al. |
| 6,165,145 A | 12/2000 | Noble |
| D439,984 S | 4/2001 | Thach |
| D440,136 S | 4/2001 | Buck |
| 6,227,959 B1 | 5/2001 | Beaudry |
| 6,228,042 B1 | 5/2001 | Dungan |
| 6,228,120 B1 | 5/2001 | Leonard et al. |
| 6,245,031 B1 | 6/2001 | Pearson |
| 6,290,660 B1 | 9/2001 | Epps et al. |
| D448,852 S | 10/2001 | Engelen |
| 6,401,289 B1 | 6/2002 | Herbert |
| 6,406,445 B1 | 6/2002 | Ben-Nun |
| 6,432,072 B1 | 8/2002 | Harris et al. |
| 6,537,236 B2 | 3/2003 | Tucek et al. |
| 6,539,328 B1 | 3/2003 | Cremonese et al. |
| D474,445 S | 5/2003 | Matsuoka |
| 6,558,338 B1 | 5/2003 | Wasserman |
| 6,568,089 B1 | 5/2003 | Popik et al. |
| D475,595 S | 6/2003 | Hatch |
| D475,679 S | 6/2003 | Cooper |
| D476,746 S | 7/2003 | Harris |
| 6,599,250 B2 | 7/2003 | Webb et al. |
| 6,599,260 B2 | 7/2003 | Tucek |
| D478,385 S | 8/2003 | Dirks |
| D481,279 S | 10/2003 | Buck |
| 6,663,657 B1 | 12/2003 | Miller |
| 6,682,496 B1 | 1/2004 | Pivaroff |
| 6,715,781 B1 | 4/2004 | Smith |
| 6,723,050 B2 | 4/2004 | Dow et al. |
| 6,723,060 B2 | 4/2004 | Miller |
| 6,758,826 B2 | 7/2004 | Luettgen et al. |
| 6,805,700 B2 | 10/2004 | Miller |
| 6,823,762 B2 | 11/2004 | Hu |
| 6,846,295 B1 | 1/2005 | Ben-Nun |
| D504,111 S | 4/2005 | Ozawa |
| D510,317 S | 10/2005 | Sun |
| 6,994,575 B1 | 2/2006 | Clark et al. |
| 7,041,072 B2 | 5/2006 | Calvert |
| D530,270 S | 10/2006 | Ozawa |
| 7,128,721 B2 | 10/2006 | Ferber et al. |
| D531,733 S | 11/2006 | Burout |
| 7,169,169 B2 | 1/2007 | Tucek et al. |
| 7,223,250 B2 | 5/2007 | Brattesani et al. |
| D544,102 S | 6/2007 | Pivaroff |
| D544,436 S | 6/2007 | Kawahara |
| D547,264 S | 7/2007 | Kondo |
| D553,252 S | 10/2007 | Masuda |
| D553,562 S | 10/2007 | Okada |
| 7,384,405 B2 | 6/2008 | Rhoades |
| D575,224 S | 8/2008 | Taniguchi |
| 7,431,706 B2 | 10/2008 | Louis |
| D579,868 S | 11/2008 | Harrison |
| D580,353 S | 11/2008 | Harrison |
| 7,470,081 B2 | 12/2008 | Miyahara et al. |
| D587,977 S | 3/2009 | Waldron |
| 7,497,639 B2 | 3/2009 | Lebot et al. |
| 7,503,923 B2 | 3/2009 | Miller |
| D593,204 S | 5/2009 | Manke |
| 7,549,966 B2 | 6/2009 | Fujii et al. |
| D597,482 S | 8/2009 | Kondo |
| D604,235 S | 11/2009 | Tarter |
| D605,586 S | 12/2009 | Tong |
| D606,192 S | 12/2009 | Summerer et al. |
| 7,731,672 B2 | 6/2010 | Chiang |
| 7,740,249 B1 | 6/2010 | Gao |
| D622,660 S | 8/2010 | Taniguchi |
| 7,857,729 B2 | 12/2010 | Sullivan et al. |
| D631,315 S | 1/2011 | Kue |
| 7,877,880 B2 | 2/2011 | Royle |
| 7,927,259 B1 | 4/2011 | Rix |
| 7,927,294 B2 | 4/2011 | Kamimura et al. |
| 7,963,717 B2 | 6/2011 | Seger |
| 7,996,996 B2 | 8/2011 | Hirabayashi |
| D649,657 S | 11/2011 | Petersen et al. |
| D658,759 S | 5/2012 | Marescaux et al. |
| D659,644 S | 5/2012 | Gretz |
| D666,303 S | 8/2012 | Ding |
| 8,313,450 B2 | 11/2012 | Ben-Nun |
| 8,342,187 B2 | 1/2013 | Kalman |
| D682,195 S | 5/2013 | Aglassinger |
| 8,435,194 B2 | 5/2013 | Dverin et al. |
| 8,479,616 B2 | 7/2013 | Tsai |
| 8,622,943 B2 | 1/2014 | Ben-Nun |
| 8,646,348 B2 | 2/2014 | Hung |
| D703,337 S | 4/2014 | Fuhr et al. |
| D703,480 S | 4/2014 | Lownds |
| 8,695,461 B2 | 4/2014 | Moss et al. |
| D706,433 S | 6/2014 | Fuhr et al. |
| D708,742 S | 7/2014 | Dallemagne et al. |
| 8,770,882 B2 | 7/2014 | Ersoy |
| 8,777,881 B2 | 7/2014 | Tsai |
| 8,864,143 B2 | 10/2014 | Lin |
| D722,016 S | 2/2015 | Beukema |
| 8,945,104 B2 | 2/2015 | Boone, III et al. |
| 8,951,216 B2 | 2/2015 | Yoo et al. |
| D726,495 S | 4/2015 | Ryan |
| 9,017,273 B2 | 4/2015 | Burbank et al. |
| D734,863 S | 7/2015 | Hennessey |
| D735,348 S | 7/2015 | Hennessey |
| 9,107,486 B2 | 8/2015 | Brewer et al. |
| 9,132,058 B2 | 9/2015 | Imboden et al. |
| 9,138,257 B2 | 9/2015 | Revivo |
| D740,222 S | 10/2015 | Tang |
| 9,272,837 B2 | 3/2016 | Linzell |
| D756,180 S | 5/2016 | Chen |
| D759,237 S | 6/2016 | Heath et al. |
| D759,238 S | 6/2016 | Heath et al. |
| 9,364,385 B2 | 6/2016 | Yang |
| D763,442 S | 8/2016 | Price et al. |
| 9,416,805 B2 | 8/2016 | Cascolan et al. |
| D776,612 S | 1/2017 | Chen |
| D778,439 S | 2/2017 | Håkansson et al. |
| 9,597,256 B1 | 3/2017 | Paul |
| 9,744,600 B2 | 8/2017 | Yang et al. |
| 9,872,813 B2 | 1/2018 | Giraud et al. |
| 9,889,066 B2 † | 2/2018 | Danby |
| D817,732 S | 5/2018 | Rettler |
| D817,869 S | 5/2018 | Lee |
| D819,221 S | 5/2018 | Lei |
| 9,981,366 B2 | 5/2018 | Todd et al. |
| D823,478 S | 7/2018 | Park |
| 10,034,813 B1 | 7/2018 | Silver |
| D826,418 S | 8/2018 | Lad |

(56) References Cited

U.S. PATENT DOCUMENTS

| | | | |
|---|---|---|---|
| D837,395 S | 1/2019 | Gan | |
| D838,378 S | 1/2019 | Cao | |
| D840,547 S | 2/2019 | Harle et al. | |
| 10,201,470 B2 | 2/2019 | Griner | |
| D842,489 S | 3/2019 | Spewock | |
| D842,491 S | 3/2019 | Fleming et al. | |
| D843,656 S | 3/2019 | Zhang et al. | |
| D844,896 S | 4/2019 | Levi et al. | |
| D847,362 S | 4/2019 | Tang | |
| D847,364 S | 4/2019 | Lee et al. | |
| 10,252,051 B2 | 4/2019 | Nichols | |
| 10,276,844 B2 | 4/2019 | Wackwitz | |
| D847,990 S | 5/2019 | Kimball | |
| 10,314,762 B1 | 6/2019 | Marton | |
| 10,335,345 B2 | 7/2019 | Choe | |
| 10,357,425 B2 | 7/2019 | Wersland et al. | |
| D855,822 S | 8/2019 | Marton | |
| D858,432 S | 9/2019 | Altenburger | |
| D862,382 S | 10/2019 | Altenburger | |
| D866,790 S | 11/2019 | Lee | |
| D867,279 S | 11/2019 | Altenburger | |
| 10,557,490 B2 | 2/2020 | Wersland et al. | |
| D877,351 S | 3/2020 | Wersland | |
| D880,419 S | 4/2020 | Hernandez et al. | |
| D880,714 S | 4/2020 | Wersland et al. | |
| D880,715 S | 4/2020 | Wersland et al. | |
| D880,716 S | 4/2020 | Wersland et al. | |
| D884,205 S | 5/2020 | Zhuang | |
| 10,702,448 B2 | 7/2020 | Wersland et al. | |
| D893,738 S | 8/2020 | Zhuang | |
| 10,758,027 B2 | 9/2020 | Skidmore et al. | |
| 10,857,064 B2 | 12/2020 | Wersland et al. | |
| 10,918,565 B2 | 2/2021 | Wersland et al. | |
| 10,945,915 B2 | 3/2021 | Wersland | |
| 10,959,908 B2 | 3/2021 | Lee et al. | |
| 10,959,911 B2 | 3/2021 | Wersland et al. | |
| D919,560 S | 5/2021 | Taniguchi | |
| 10,993,874 B1 | 5/2021 | Marton et al. | |
| 11,160,721 B2 * | 11/2021 | Wersland | A61H 15/00 |
| 11,160,723 B2 | 11/2021 | Wersland et al. | |
| 11,478,400 B1 | 10/2022 | Marton et al. | |
| 11,478,606 B1 | 10/2022 | English et al. | |
| 2001/0016697 A1 | 8/2001 | Gorsen | |
| 2001/0027280 A1 | 10/2001 | Huang | |
| 2002/0082532 A1 | 6/2002 | Tucek et al. | |
| 2002/0115947 A1 | 8/2002 | Young | |
| 2002/0177795 A1 | 11/2002 | Frye | |
| 2002/0183668 A1 | 12/2002 | Huang | |
| 2002/0188233 A1 | 12/2002 | Denyes | |
| 2003/0009116 A1 | 1/2003 | Luettgen | |
| 2003/0014079 A1 | 1/2003 | Tucek | |
| 2003/0028134 A1 | 2/2003 | Lev et al. | |
| 2003/0094356 A1 | 5/2003 | Waldron | |
| 2003/0144615 A1 | 7/2003 | Lin | |
| 2003/0195443 A1 | 10/2003 | Miller | |
| 2004/0176710 A1 | 9/2004 | Kennedy et al. | |
| 2005/0075591 A1 | 4/2005 | Hafemann | |
| 2005/0109137 A1 * | 5/2005 | Hartmann | B23D 51/16 74/25 |
| 2005/0113870 A1 | 5/2005 | Miller | |
| 2005/0126018 A1 | 6/2005 | Haas | |
| 2005/0131461 A1 | 6/2005 | Tucek et al. | |
| 2005/0203445 A1 | 9/2005 | Tsai | |
| 2005/0235988 A1 | 10/2005 | Hansen et al. | |
| 2005/0252011 A1 | 11/2005 | Neumeier | |
| 2006/0025710 A1 | 2/2006 | Schulz | |
| 2006/0047315 A1 | 3/2006 | Colloca et al. | |
| 2006/0074455 A1 | 4/2006 | Strandberg | |
| 2006/0116614 A1 | 6/2006 | Jones et al. | |
| 2006/0118841 A1 | 6/2006 | Eliason et al. | |
| 2006/0123941 A1 | 6/2006 | Wadge | |
| 2006/0192527 A1 | 8/2006 | Kageler | |
| 2006/0211961 A1 | 9/2006 | Meyer et al. | |
| 2006/0272664 A1 | 12/2006 | O'Dwyer | |
| 2007/0129220 A1 | 6/2007 | Bardha | |
| 2007/0144310 A1 | 6/2007 | Pozgay | |
| 2007/0150004 A1 | 6/2007 | Colloca | |
| 2007/0173886 A1 | 7/2007 | Rousso et al. | |
| 2007/0179414 A1 | 8/2007 | Imboden et al. | |
| 2007/0270727 A1 | 11/2007 | Khorassani Zadeh | |
| 2007/0282228 A1 | 12/2007 | Einav et al. | |
| 2008/0077061 A1 | 3/2008 | Dehli | |
| 2008/0097260 A1 | 4/2008 | Tsukada et al. | |
| 2008/0103419 A1 | 5/2008 | Adamson | |
| 2008/0146980 A1 | 6/2008 | Rousso et al. | |
| 2008/0167588 A1 | 7/2008 | Chen | |
| 2008/0169715 A1 | 7/2008 | Mills | |
| 2008/0177207 A1 | 7/2008 | Liao | |
| 2008/0185888 A1 | 8/2008 | Beall et al. | |
| 2008/0200849 A1 | 8/2008 | Hollington | |
| 2008/0243041 A1 | 10/2008 | Brenner et al. | |
| 2008/0306417 A1 | 12/2008 | Imboden et al. | |
| 2008/0312568 A1 | 12/2008 | Chen | |
| 2008/0314610 A1 | 12/2008 | Meixner | |
| 2009/0112134 A1 | 4/2009 | Avni | |
| 2009/0188119 A1 | 7/2009 | Oberheim | |
| 2009/0270777 A1 | 10/2009 | Wu et al. | |
| 2009/0309313 A1 | 12/2009 | Knorr et al. | |
| 2009/0326540 A1 | 12/2009 | Estes | |
| 2010/0100119 A1 | 4/2010 | Herndon | |
| 2010/0137907 A1 | 6/2010 | Tsai | |
| 2010/0145242 A1 | 6/2010 | Tsai | |
| 2010/0160841 A1 | 6/2010 | Wu | |
| 2010/0162579 A1 | 7/2010 | Naughton et al. | |
| 2010/0176919 A1 | 7/2010 | Myers et al. | |
| 2010/0210194 A1 | 8/2010 | Thomaschewski et al. | |
| 2010/0274162 A1 | 10/2010 | Evans | |
| 2010/0286569 A1 | 11/2010 | Nagano | |
| 2010/0298863 A1 | 11/2010 | Hindinger et al. | |
| 2011/0037431 A1 | 2/2011 | Mackle | |
| 2011/0055720 A1 | 3/2011 | Potter et al. | |
| 2011/0118637 A1 | 5/2011 | Lev et al. | |
| 2011/0201979 A1 | 8/2011 | Voss et al. | |
| 2011/0224580 A1 | 9/2011 | Leathers et al. | |
| 2011/0314677 A1 | 12/2011 | Meier et al. | |
| 2012/0059294 A1 | 3/2012 | Schubert et al. | |
| 2012/0065556 A1 | 3/2012 | Smith et al. | |
| 2012/0078071 A1 | 3/2012 | Bohm et al. | |
| 2012/0124758 A1 | 5/2012 | Sabisch et al. | |
| 2012/0161706 A1 | 6/2012 | Zhou | |
| 2012/0197357 A1 | 8/2012 | Dewey et al. | |
| 2012/0232445 A1 | 9/2012 | Lev et al. | |
| 2012/0238922 A1 | 9/2012 | Stemple et al. | |
| 2012/0253245 A1 | 10/2012 | Stanbridge | |
| 2013/0014968 A1 | 1/2013 | Kehoe et al. | |
| 2013/0030506 A1 | 1/2013 | Bartolone et al. | |
| 2013/0046212 A1 | 2/2013 | Nichols | |
| 2013/0052871 A1 | 2/2013 | Eklind | |
| 2013/0085421 A1 | 4/2013 | Gillespie et al. | |
| 2013/0116503 A1 | 5/2013 | Mertens et al. | |
| 2013/0133210 A1 | 5/2013 | Weir | |
| 2013/0138023 A1 | 5/2013 | Lerro | |
| 2013/0218058 A1 | 8/2013 | Ceoldo et al. | |
| 2013/0237751 A1 | 9/2013 | Alexander | |
| 2013/0241470 A1 | 9/2013 | Kim | |
| 2013/0261516 A1 | 10/2013 | Cilea | |
| 2013/0261517 A1 | 10/2013 | Rodgers | |
| 2013/0271067 A1 | 10/2013 | Yu et al. | |
| 2013/0281897 A1 * | 10/2013 | Hoffmann | A61H 23/00 601/107 |
| 2013/0304642 A1 | 11/2013 | Campos | |
| 2014/0024982 A1 | 1/2014 | Doyle | |
| 2014/0031866 A1 | 1/2014 | Fuhr et al. | |
| 2014/0097793 A1 | 4/2014 | Wurtz et al. | |
| 2014/0101872 A1 | 4/2014 | Utsch et al. | |
| 2014/0163443 A1 | 6/2014 | Young et al. | |
| 2014/0180331 A1 | 6/2014 | Turner | |
| 2014/0190023 A1 * | 7/2014 | Vitantonio | B23D 51/16 83/838 |
| 2014/0194900 A1 | 7/2014 | Sedic | |
| 2014/0200495 A1 | 7/2014 | Jones | |
| 2014/0207032 A1 | 7/2014 | Dematio et al. | |
| 2014/0209594 A1 | 7/2014 | Besner | |
| 2014/0221887 A1 | 8/2014 | Wu | |

(56) References Cited

U.S. PATENT DOCUMENTS

| | | |
|---|---|---|
| 2014/0288473 A1 | 9/2014 | Matsushita |
| 2014/0305747 A1 | 10/2014 | Kumar et al. |
| 2014/0310900 A1 | 10/2014 | Curry et al. |
| 2014/0316313 A1 | 10/2014 | Mayer et al. |
| 2015/0005682 A1* | 1/2015 | Danby ............ A61H 23/0254 601/101 |
| 2015/0042254 A1 | 2/2015 | Kato |
| 2015/0082562 A1 | 3/2015 | Kamada |
| 2015/0098184 A1 | 4/2015 | Tsai et al. |
| 2015/0119771 A1 | 4/2015 | Roberts |
| 2015/0133833 A1 | 5/2015 | Bradley et al. |
| 2015/0145297 A1 | 5/2015 | Lee |
| 2015/0148592 A1 | 5/2015 | Kanbar |
| 2015/0157528 A1 | 6/2015 | Le et al. |
| 2015/0176674 A1 | 6/2015 | Khan et al. |
| 2015/0216719 A1 | 8/2015 | DeBenedictis et al. |
| 2015/0257964 A1 | 9/2015 | Ajiki |
| 2015/0305969 A1 | 10/2015 | Giraud et al. |
| 2015/0328081 A1 | 11/2015 | Goldenberg et al. |
| 2015/0375315 A1 | 12/2015 | Ukai |
| 2016/0000642 A1 | 1/2016 | Zipper |
| 2016/0017905 A1 | 1/2016 | Cascolan et al. |
| 2016/0030279 A1 | 2/2016 | Driscoll et al. |
| 2016/0045661 A1 | 2/2016 | Gray et al. |
| 2016/0112841 A1 | 4/2016 | Holland |
| 2016/0113840 A1 | 4/2016 | Crunick et al. |
| 2016/0113841 A1 | 4/2016 | Godfrey et al. |
| 2016/0127129 A1 | 5/2016 | Chee et al. |
| 2016/0129186 A1 | 5/2016 | Douglas et al. |
| 2016/0136037 A1 | 5/2016 | Cai |
| 2016/0136040 A1 | 5/2016 | Li |
| 2016/0166464 A1 | 6/2016 | Douglas et al. |
| 2016/0170996 A1 | 6/2016 | Frank et al. |
| 2016/0192814 A1 | 7/2016 | Kang et al. |
| 2016/0206502 A1 | 7/2016 | Køltzow |
| 2016/0243359 A1 | 8/2016 | Sharma |
| 2016/0263732 A1 | 9/2016 | Lourenco et al. |
| 2016/0269486 A1 | 9/2016 | Gupta et al. |
| 2016/0310353 A1 | 10/2016 | Barasch |
| 2016/0311091 A1 | 10/2016 | Wang |
| 2016/0324717 A1 | 11/2016 | Burton |
| 2016/0338901 A1 | 11/2016 | Cohen |
| 2016/0346163 A1 | 12/2016 | Konik et al. |
| 2016/0367425 A1 | 12/2016 | Wersland |
| 2017/0027798 A1† | 2/2017 | Wersland |
| 2017/0042754 A1 | 2/2017 | Fowers et al. |
| 2017/0049278 A1 | 2/2017 | Thomassen |
| 2017/0069191 A1 | 3/2017 | Erkkila |
| 2017/0119623 A1 | 5/2017 | Attarian |
| 2017/0128320 A1 | 5/2017 | Chen |
| 2017/0156974 A1 | 6/2017 | Griner |
| 2017/0156975 A1 | 6/2017 | Mills |
| 2017/0189227 A1 | 7/2017 | Brunson et al. |
| 2017/0216136 A1 | 8/2017 | Gordon |
| 2017/0233063 A1 | 8/2017 | Zhao et al. |
| 2017/0246074 A1 | 8/2017 | Wu |
| 2017/0304144 A1 | 10/2017 | Tucker |
| 2017/0304145 A1 | 10/2017 | Pepe |
| 2017/0312161 A1 | 11/2017 | Johnson et al. |
| 2017/0360641 A1 | 12/2017 | Nakata et al. |
| 2018/0008512 A1 | 1/2018 | Goldstein |
| 2018/0050440 A1 | 2/2018 | Chen |
| 2018/0078449 A1 | 3/2018 | Callow |
| 2018/0133101 A1 | 5/2018 | Inada |
| 2018/0140100 A1 | 5/2018 | Cribbs |
| 2018/0140502 A1 | 5/2018 | Shahoian et al. |
| 2018/0141188 A1 | 5/2018 | Lai |
| 2018/0154141 A1 | 6/2018 | Ahn |
| 2018/0185234 A1 | 7/2018 | Ishiguro et al. |
| 2018/0200141 A1 | 7/2018 | Wersland |
| 2018/0236572 A1 | 8/2018 | Ukai |
| 2018/0243158 A1 | 8/2018 | Loghmani |
| 2018/0263845 A1 | 9/2018 | Wersland et al. |
| 2018/0279843 A1 | 10/2018 | Paul |
| 2018/0288160 A1 | 10/2018 | Paul et al. |
| 2018/0296433 A1 | 10/2018 | Danby |
| 2018/0315499 A1 | 11/2018 | Appelbaum et al. |
| 2018/0315504 A1 | 11/2018 | Inada et al. |
| 2019/0000709 A1 | 1/2019 | Sone et al. |
| 2019/0038229 A1 | 2/2019 | Perraut et al. |
| 2019/0066833 A1 | 2/2019 | Wicki |
| 2019/0110945 A1 | 4/2019 | Kawagoe et al. |
| 2019/0175434 A1 | 6/2019 | Zhang |
| 2019/0209424 A1 | 7/2019 | Wersland et al. |
| 2019/0216677 A1 | 7/2019 | Paul |
| 2019/0232478 A1 | 8/2019 | Zawisza et al. |
| 2019/0254921 A1 | 8/2019 | Marton et al. |
| 2019/0254922 A1 | 8/2019 | Marton et al. |
| 2019/0314239 A1 | 10/2019 | Ci |
| 2019/0337140 A1 | 11/2019 | Shanklin |
| 2019/0350793 A1 | 11/2019 | Wersland et al. |
| 2019/0381271 A1 | 12/2019 | Jo |
| 2020/0000237 A1 | 1/2020 | Wu |
| 2020/0009010 A1 | 1/2020 | Park et al. |
| 2020/0016027 A1 | 1/2020 | Kim et al. |
| 2020/0035237 A1 | 1/2020 | Kim et al. |
| 2020/0069510 A1 | 3/2020 | Wersland et al. |
| 2020/0085675 A1 | 3/2020 | Lee et al. |
| 2020/0090175 A1 | 3/2020 | Davis et al. |
| 2020/0179210 A1 | 6/2020 | Barragan Gomez |
| 2020/0179215 A1 | 6/2020 | Lerner |
| 2020/0230012 A1 | 7/2020 | Fuhr |
| 2020/0241683 A1 | 7/2020 | Le et al. |
| 2020/0261306 A1 | 8/2020 | Pepe |
| 2020/0261307 A1 | 8/2020 | Nersland |
| 2020/0268594 A1 | 8/2020 | Pepe |
| 2020/0294423 A1 | 9/2020 | Blain et al. |
| 2020/0352821 A1 | 11/2020 | Wersland et al. |
| 2020/0390644 A1 | 12/2020 | Yang |
| 2020/0397651 A1 | 12/2020 | Park et al. |
| 2020/0405570 A1 | 12/2020 | Kodama |
| 2021/0000683 A1 | 1/2021 | Cheng |
| 2021/0022951 A1 | 1/2021 | Hu |
| 2021/0022955 A1 | 1/2021 | Wersland et al. |
| 2021/0059898 A1 | 3/2021 | Wersland et al. |
| 2021/0085555 A1 | 3/2021 | Davis et al. |
| 2021/0128402 A1 | 5/2021 | Dai et al. |
| 2021/0330539 A9 | 10/2021 | Faussett |
| 2022/0000781 A9 | 1/2022 | Leneweit et al. |
| 2022/0007810 A1 | 1/2022 | Paspatis et al. |
| 2022/0054350 A1 | 2/2022 | Merino et al. |
| 2022/0087433 A1 | 3/2022 | Mao et al. |
| 2022/0241135 A1 | 8/2022 | Wang |
| 2023/0001131 A1 | 1/2023 | English et al. |

FOREIGN PATENT DOCUMENTS

| | | |
|---|---|---|
| CN | 86101310 A | 9/1986 |
| CN | 1432452 A | 7/2003 |
| CN | 2788807 | 6/2006 |
| CN | 201239336 Y | 5/2009 |
| CN | 201239338 Y | 5/2009 |
| CN | 201333160 Y | 10/2009 |
| CN | 201524220 U | 7/2010 |
| CN | 101888050 A | 11/2010 |
| CN | 201743890 U | 2/2011 |
| CN | 201847899 U | 6/2011 |
| CN | 301664182 S | 9/2011 |
| CN | 202161539 U | 3/2012 |
| CN | 202637439 U | 1/2013 |
| CN | 103648320 A | 3/2014 |
| CN | 203598194 U | 5/2014 |
| CN | 303250924 S | 6/2015 |
| CN | 303250929 S | 6/2015 |
| CN | 205163583 U | 4/2016 |
| CN | 104352341 | 7/2016 |
| CN | 104352341 B | 7/2016 |
| CN | 205459750 U | 8/2016 |
| CN | 205494357 U | 8/2016 |
| CN | 205598186 U | 9/2016 |
| CN | 106074129 A | 11/2016 |
| CN | 106236528 A | 12/2016 |
| CN | 206081000 U | 4/2017 |
| CN | 106859949 A | 6/2017 |

(56) References Cited

FOREIGN PATENT DOCUMENTS

| | | |
|---|---|---|
| CN | 304561844 S | 3/2018 |
| CN | 207286298 U | 5/2018 |
| CN | 207855923 U | 9/2018 |
| CN | 109259995 A | 1/2019 |
| CN | 208405314 U | 1/2019 |
| CN | 208448086 U | 2/2019 |
| CN | 109528473 A | 3/2019 |
| CN | 209154392 U | 7/2019 |
| CN | 110868983 A | 3/2020 |
| CN | 106618998 B | 8/2020 |
| CN | 111616938 A | 9/2020 |
| CN | 111973419 A | 11/2020 |
| CN | 113143721 A | 7/2021 |
| CN | 113509366 A | 10/2021 |
| DE | 3633888 A1 | 4/1988 |
| DE | 19905199 A1 | 7/2000 |
| DE | 102015102112 A1 | 8/2015 |
| DE | 202015005257 U1 | 10/2016 |
| EP | 0436719 B1 | 5/1994 |
| EP | 1728494 A1 | 12/2006 |
| EP | 2080500 A1 | 7/2009 |
| EP | 2328255 A1 | 6/2011 |
| EP | 1728494 B1 | 1/2013 |
| GB | 2066081 A | 7/1981 |
| GB | 2262236 A | 6/1993 |
| JP | S5230553 A | 3/1977 |
| JP | S5428491 A | 3/1979 |
| JP | 1990019157 | 1/1990 |
| JP | H03218763 A | 9/1991 |
| JP | H048128 B2 | 2/1992 |
| JP | H0447440 A | 2/1992 |
| JP | 1992047440 | 4/1992 |
| JP | 1995051393 | 2/1995 |
| JP | 2000189525 A | 7/2000 |
| JP | 003077837 | 6/2001 |
| JP | 2002282322 A | 10/2002 |
| JP | 2003077837 A | 3/2003 |
| JP | 2005204777 | 4/2005 |
| JP | 2006034941 A | 2/2006 |
| JP | 2006212228 A | 8/2006 |
| JP | 2008510588 A | 4/2008 |
| JP | 2008289616 A | 12/2008 |
| JP | 2010534110 | 11/2010 |
| JP | 2011502369 A | 1/2011 |
| JP | 5129032 B2 | 1/2013 |
| JP | 2013119018 A | 6/2013 |
| JP | 2014511240 A | 5/2014 |
| JP | 2015035844 A | 2/2015 |
| JP | 2015104422 A | 6/2015 |
| JP | 2018518347 A | 7/2018 |
| KR | 200313149 Y1 | 5/2003 |
| KR | 200435552 Y1 | 1/2007 |
| KR | 100752432 B1 | 8/2007 |
| KR | 20090119424 A | 11/2009 |
| KR | 101123926 | 4/2012 |
| KR | 101162978 B1 | 7/2012 |
| KR | 101406275 | 6/2014 |
| KR | 20170106550 A | 9/2017 |
| KR | 20170108550 A | 9/2017 |
| KR | 20180031683 A | 3/2018 |
| KR | 20200051098 A | 5/2020 |
| RU | 2170567 C1 | 7/2001 |
| TW | I359657 B | 3/2012 |
| TW | 201440753 A | 8/2015 |
| WO | WO-0119316 A2 | 3/2001 |
| WO | 2009014727 | 1/2009 |
| WO | WO-2009102279 A1 | 8/2009 |
| WO | WO-2011159317 A1 | 12/2011 |
| WO | WO-2013114084 A1 | 8/2013 |
| WO | WO-2013145346 A1 | 10/2013 |
| WO | 2014118596 | 8/2014 |
| WO | 2015038005 | 3/2015 |
| WO | WO-2018012105 A1 | 1/2018 |
| WO | WO-2019186225 A1 | 10/2019 |
| WO | WO-2021050861 A1 | 3/2021 |
| WO | WO-2023172676 A2 | 9/2023 |

OTHER PUBLICATIONS

TheraGun device in Archive.org webpage https://web.archive.org/web/20151218063848/ http://www.theragun.com/#intro-1 Dec. 18, 2015 (archive date).

TheraGun G1 device in YouTube video "Theragun G1: Product Overview," https://www.youtube.com/watch?v=m9ilhfMGfZ8 Apr. 18, 2017 (upload date).

TheraGun G2Pro device in YouTube video "The Theragun G2PRO: Revolutionary Percussive Therapy," https://www.youtube.com/watch?v=2p9R6VA798o Oct. 10, 2017 (upload date).

TheraGun device in YouTube video "TheraGun Demo," https://www.youtube.com/watch?v=l186_6naJnk Aug. 14, 2017 (upload date).

PCT/US2016/038326 International Search Report & Written Opinion dated Sep. 1, 2016.

PCT/US2018/022426 International Search Report & Written Opinion dated May 31, 2018.

AU 2016284030 Examination Report dated May 7, 2018.

JP2018-517683 Office Action dated Oct. 25, 2018.

CA 2990178 Office Action dated Oct. 25, 2018.

WORX Trans4mer "Safety and Operating Manual Original Instructions" for 12V Li-Ion Multi-purpose saw, WX540, WX540.3, WX540.9, 2013.

Rachel [no family name indicated], "Jigsaw Massager", Apr. 18, 2010 (https://web.archive.org/web/20100418041422/http://www.instructables.com/id/Jigsaw-Massager/).

Rockwell Trans4mer Operating Manual for Multi-purpose saw, Model RK2516/RK2516K, 2011.

PCT/US2020/031936 International Search Report & Written Opinion dated Sep. 11, 2020.

PCT/US2020/50399 International Search Report & Written Opinion dated Feb. 4, 2021.

Amazon: "OIVO Xbox One Controller Charger Dual Charging Station Updated Strap, Remote Charger Dock-2 Rechargeable Battery Packs Included," OIVO, Sep. 6, 2018, Especially annotated figures, Retrieved from Entire Document, 11 Pages.

Amazon: "PowerA Joy Con & Pro Controller Charging Dock Nintendo Switch," PowerA, Oct. 31, 2017, Especially annotated figures, Retrieved from Entire Document, 10 Pages.

Amazon: "Theragun G3PRO Percussive Therapy Device, White, Handheld Deep Muscle, Treatment Massager & Muscle Stimulator for Pain Relief, Recovery, Enhance Performance & Energize The Body," Feb. 13, 2019, Shown on pp. 1, 2 Pages, Retrieved from URL: https://www.amazon.com/dp/B07MJ2MCT3/ref=nav_timeline_asin?_encoding=UTF8&psc=1.

Anthony Katz, "The RAPTOR: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Bardwell D., "Wahl's Massage Products—Meant for Life's Big Pains," DougBardwell.com, Apr. 6, 2016, 7 Pages, [Retrieved on Jun. 3, 2021] Retrieved from URL: https://dougbardwell.com/db/2016/04/06/wahls-massage-products-meant-for-lifes-big-pains/.

Collins D., "External Rotor Motor Basics: Design and Applications," Jun. 6, 2018, 03 Pages.

Collins D., "FAQ: What are Hall Effect Sensors and What Is Theirs Role in DC Motors?," Jan. 11, 2017, 03 Pages.

Defendant's Initial Invalidity Contentions, *Therabody, Inc.* v. *Tzumi Electronics LLC* et al., Case No. SDNY-1-21-cv-07803 (PGG)(RWL), dated Aug. 17, 2022; 16 pages.

Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).

Digi-key's North American Editors: "How to Power and Control Brushless DC Motors," Dec. 7, 2016, 09 Pages.

(56) References Cited

OTHER PUBLICATIONS

Extended European Search Report for European Application No. 16815104.1, dated Jan. 23, 2019, 08 Pages.
Extended European Search Report for European Application No. 18832213.5, dated Jul. 21, 2021, 11 Pages.
Extended European Search Report for European Application No. 18832923.9, dated Apr. 23, 2021, 7 Pages.
Extended European Search Report for European Application No. 20720323.3, dated Sep. 9, 2021, 10 Pages.
Extended European Search Report for European Application No. 20802710.2, dated May 10, 2022, 9 Pages.
Extended European Search Report for European Application No. 20802804.3, dated Apr. 28, 2022, 8 Pages.
Extended European Search Report for European Application No. 21178300.6, dated Oct. 19, 2021, 9 Pages.
Extended European Search Report for European Application No. 21178311.3, dated Sep. 23, 2021, 5 Pages.
Holly Riddle, "Theragun vs. Hyperice vs. Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.
International Preliminary Report on Patentability for International Application No. PCT/US2016/038326, dated Jan. 4, 2018, 8 Pages.
International Preliminary Report on Patentability for International Application No. PCT/US2018/022426, dated Sep. 26, 2019, 9 Pages.
International Preliminary Report on Patentability for International Application No. PCT/US2018/039599, dated Jan. 23, 2020, 8 Pages.
International Preliminary Report on Patentability for International Application No. PCT/US2018/040795, dated Jan. 23, 2020, 7 Pages.
International Preliminary Report on Patentability for International Application No. PCT/US2019/067624, dated Jul. 8, 2021, 11 Pages.
International Preliminary Report on Patentability for International Application No. PCT/US2020/017645, dated Aug. 26, 2021, 11 Pages.
International Preliminary Report on Patentability for International Application No. PCT/US2020/031339, dated Nov. 18, 2021, 11 Pages.
International Preliminary Report on Patentability for International Application No. PCT/US2020/031936, dated Nov. 18, 2021, 14 Pages.
International Preliminary Report on Patentability for International Application No. PCT/US2020/050385, dated Mar. 24, 2022, 12 Pages.
International Preliminary Report on Patentability for International Application No. PCT/US2020/050399, dated Jan. 13, 2022, 6 Pages.
International Preliminary Report on Patentability for International Application No. PCT/US2020/054773, dated Apr. 21, 2022, 8 Pages.
International Preliminary Report on Patentability for International Application No. PCT/US2020/054842, dated Apr. 21, 2022, 7 Pages.
International Preliminary Report on Patentability for International Application No. PCT/US2020/063426, dated Jun. 16, 2022, 06 Pages.
International Preliminary Report on Patentability for International Application No. PCT/US2021/022500, dated Oct. 6, 2022, 6 Pages.
International Preliminary Report on Patentability for International Application No. PCT/US2021/029900, dated Nov. 10, 2022, 9 Pages.
International Preliminary Report on Patentability for International Application No. PCT/US2021/029903, dated Nov. 10, 2022, 7 Pages.
International Search Report and Written Opinion for International Application No. PCT/US2018/039599, dated Sep. 24, 2018, 9 Pages.
International Search Report and Written Opinion for International Application No. PCT/US2018/040795, dated Sep. 24, 2018, 8 Pages.
International Search Report and Written Opinion for International Application No. PCT/US2019/067624, dated Feb. 3, 2020, 13 Pages.
International Search Report and Written Opinion for International Application No. PCT/US2020/017645, dated May 20, 2020, 13 Pages.
International Search Report and Written Opinion for International Application No. PCT/US2020/031339, dated Jun. 10, 2020, 12 Pages.
International Search Report and Written Opinion for International Application No. PCT/US2020/031347, dated Aug. 3, 2020, 9 Pages.
International Search Report and Written Opinion for International Application No. PCT/US2020/050385, dated Dec. 3, 2020, 13 Pages.
International Search Report and Written Opinion for International Application No. PCT/US2020/054773, dated Jan. 12, 2021, 9 Pages.
International Search Report and Written Opinion for International Application No. PCT/US2020/054842, dated Jan. 11, 2021, 8 Pages.
International Search Report and Written Opinion for International Application No. PCT/US2020/063426, dated Feb. 26, 2021, 09 Pages.
International Search Report and Written Opinion for International Application No. PCT/US2021/022500, dated Apr. 20, 2021, 7 Pages.
International Search Report and Written Opinion for International Application No. PCT/US2021/029900, dated Oct. 6, 2021, 12 Pages.
International Search Report and Written Opinion for International Application No. PCT/US2021/029903, dated Jul. 28, 2021, 8 Pages.
International Search Report and Written Opinion for International Application No. PCT/US2022/028309, dated Sep. 8, 2022, 10 Pages.
International Search Report and Written Opinion for International Application No. PCT/US2022/076238, dated Jan. 23, 2023, 12 Pages.
Machine translation from Espacenet of written description and claims for CN106074129A, 9 pages (2016).
Machine translation from Espacenet of written description and claims for CN111616938A, 5 pages (2020).
Machine translation from Espacenet of written description and claims for CN111973419A, 7 pages (2020).
Machine Translation of Written Description and Claims for WO2013145346A1 (Year: 2013).
Massage Expert: "Nursal Deep Percussion Massager Review—6 Interchangeable Nodes," Jan. 4, 2021, 6 Pages, [Retrieved on Jun. 3, 2021] Retrieved from URL: https://www.massageexpert.net/nursal-deep-percussion-massager-review/.
McFarland M., "Segway Was Supposed to Change the World, Two Decades Later, It Just Might," CNN Wire Service, Oct. 30, 2018, 7 Pages.
Partial Supplementary European Search Report for European Application No. 18832213.5, dated Apr. 20, 2021, 12 Pages.
Supplementary European Search Report for European Application No. 19904459.5, dated Apr. 15, 2021, 04 Pages.
Testberichte.de: "Naipo Handheld Percussion Massager with Heating (MGPC 5000)," amazon.de, 7 Pages, [Retrieved on Jun. 3, 2021] Retrieved from URL: https://www.testberichte.de/p/naipo-tests/handheld-percussion-massager-with-heating-mgpc-5000-testbericht.html, See also a YouTube Review of this Device dated May 21, 2018 at https://www.youtube.com/watch?v=bi_QCJA3D9k.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Visual Description of Hyper Ice, Inc. Raptor Device, "RAPTOR Solutions 1.3 Prone," available at: https://www.youtube.com/watch?v=6i1tRqdwPU8&t=156s (last visited Feb. 15, 2023); 1 page.

(56) References Cited

OTHER PUBLICATIONS

WORX Trans4mer "Safety and Operating Manual Original Instructions" for 12V Li-Ion Multipurpose saw, WX540, NX540.3, WX540.9, 16 pages (2013).
Youtube: "Unboxing: Joy-Con & Pro Controller Charging Dock for Nintendo Switch," Crusherbad64, Especially demonstration 8:30-8:55, (This reference is Being Used to Show Greater Details of Product not Clearly Disclosed in 'PowerA'), Feb. 26, 2018, Retrieved from entire document, 1 Page.

\* cited by examiner
† cited by third party

PERCUSSIVE THERAPY DEVICE WITH VARIABLE AMPLITUDE

CROSS-REFERENCE TO RELATED APPLICATIONS

This application is a continuation of U.S. patent application Ser. No. 17/018,044, filed Sep. 11, 2020, which is a continuation-in-part of U.S. patent application Ser. No. 16/869,402, filed May 7, 2020, now U.S. Pat. No. 10,857,064, which is a continuation-in-part of U.S. patent application Ser. No. 16/675,772, filed Nov. 6, 2019, now U.S. Pat. No. 10,702,448, which is a continuation-in-part of U.S. patent application Ser. No. 16/357,984, filed Mar. 19, 2019, now U.S. Pat. No. 10,912,707, which is a continuation of U.S. patent application Ser. No. 15/920,322, filed on Mar. 13, 2018, now U.S. Pat. No. 10,357,425, which is a continuation-in-part of U.S. patent application Ser. No. 15/458,920, filed on Mar. 14, 2017, which is a continuation-in-part of Ser. No. 15/186,859, filed on Jun. 20, 2016, which claims the benefit of U.S. Provisional Patent Application No. 62/182,525, filed on Jun. 20, 2015. U.S. patent application Ser. No. 16/675,772 also claims the benefit of U.S. Provisional Patent Application No. 62/785,151, filed on Dec. 26, 2018, U.S. Provisional Patent Application No. 62/844,424, filed on May 7, 2019, and U.S. Provisional Patent Application No. 62/899,098, filed on Sep. 11, 2019. U.S. patent application Ser. No. 16/869,402 also claims the benefit of U.S. Patent Application No. 63/044,860, filed Jun. 26, 2020 and U.S. Patent Application No. 63/065,114, filed Aug. 13, 2020. All applications listed above are incorporated by reference herein in their entireties.

FIELD OF THE INVENTION

The present invention relates generally to massage devices and more particularly to a percussive therapy device with variable amplitude.

BACKGROUND OF THE INVENTION

Percussive massage devices typically only include a single reciprocating amplitude or stroke. However, different amplitudes may provide different levels or types of massage. Accordingly, a need exists for a percussive massage device with the ability to vary the amplitude.

SUMMARY OF THE PREFERRED EMBODIMENTS

In accordance with a first aspect of the present invention there is provided a percussive therapy device that includes a housing, an electrical source, a motor positioned in the housing, a switch for activating the motor, a push rod assembly operatively connected to the motor and configured to provide reciprocating motion in response to activation of the motor, and a massage attachment secured to a distal end of the push rod assembly. The reciprocating motion of the push rod assembly has a user-adjustable amplitude. In a preferred embodiment, the distal end of the push rod assembly reciprocates within a first range and the amplitude is user-adjustable such that the distal end reciprocates within a second range. The second range is different than the first range. In a preferred embodiment, the device includes an input that changes the amplitude from the first range to the second range.

In a preferred embodiment, the percussive therapy device includes a variable amplitude assembly that includes an eccentric weight member. The eccentric weight member is operatively connected to the motor. In an embodiment, the motor includes a motor shaft operatively connected to the eccentric weight member. In another embodiment, the eccentric weight member may include a shaft that is received in the motor. The motor is configured to rotate the eccentric weight member about a first axis in a first direction and an opposite second direction. When the eccentric weight member is rotated in the first direction the distal end of the push rod assembly reciprocates within the first range, and when the eccentric weight member is rotated in the second direction the distal end of the push rod assembly reciprocates within the second range. Preferably, the variable amplitude assembly includes a movable member that is movable with respect to the eccentric weight member between a first position and a second position. The movable member includes an offset shaft extending therefrom to which the push rod assembly is operatively connected. The distal end of the push rod assembly reciprocates within the first range when the movable member is in the first position and the distal end of the push rod assembly reciprocates within the second range when the movable member is in the second position. The movable member is movable from the first position to the second position when the rotation of the eccentric weight and/or motor shaft is reversed from the first direction to the second direction and vice versa. Preferably, at least one slot is defined in the eccentric weight member. The movable member includes a main body portion with a slide member extending therefrom. The slide member is received in and movable within the slot. In another embodiment, the movable member can include the slot and the slide member can extend from the eccentric weight member.

In a preferred embodiment, the variable amplitude device includes an interference member that is positioned in a channel defined in the eccentric weight member. The interference member is movable between a deployed position and a rest position. In one of the deployed position or the rest position the interference member prevents the movable member from moving between the first position and the second position, and in the other of the deployed position and the rest position the interference member does not prevent the movable member from moving between the first position and the second position. In an embodiment where in the deployed position the interference member prevents the movable member from moving between the first position and the second position and in the rest position the interference member does not prevent the movable member from moving between the first position and the second position, the interference member is biased to the rest position by a spring. In this embodiment, the interference member is movable from the rest position to the deployed position when the eccentric weight member and/or motor shaft rotates at a predetermined RPM. This movement is due to the weight of the interference member and the centripetal force created as rotational speed increases. In a preferred embodiment, the interference member includes a stop member and the movable member includes a tooth. In the deployed position the stop member blocks the tooth to prevent the movable member from moving between the first position and the second position.

In a preferred embodiment, the interference member is movable from the rest position to the deployed position (or vice versa) by the activation of an electromagnet. In the embodiment with the electromagnet, the interference member may include a stop member and the movable member includes a tooth, and in the rest position the stop member blocks the tooth to prevent the movable member from moving between the first position and the second position.

In accordance with another aspect of the present invention there is provided a method of using a percussive therapy device that includes a housing, an electrical source, a motor positioned in the housing, a switch for activating the motor, a push rod assembly operatively connected to the motor and configured to provide reciprocating motion in response to activation of the motor, and a massage attachment secured to a distal end of the push rod assembly. The method includes (a) activating the motor and massaging a body part with the massage attachment, where the distal end of the push rod assembly reciprocates within a first range, (b) adjusting an amplitude of the reciprocation, and (c) activating the motor and massaging the body part with the massage attachment, where the distal end of the push rod assembly reciprocates within a second range. The second range is different than the first range. In a preferred embodiment, the method includes the step of activating an input to adjust the amplitude. In a preferred embodiment, the motor includes a motor shaft, wherein during step (a) the motor shaft is rotated in a first direction, and wherein during step (c) the motor shaft is rotated in a second direction. In a preferred embodiment, the device includes an eccentric weight member that is rotated by the motor, wherein during step (a) the eccentric weight member is rotated in a first direction, and wherein during step (c) the eccentric weight member is rotated in a second direction. Preferably, the input causes the change in direction of the motor, thereby causing the amplitude to be varied.

In accordance with another aspect of the present invention there is provided a variable amplitude assembly that includes an eccentric weight member that is rotatable about a first axis in a first direction and an opposite second direction, and a movable member that is movable with respect to the eccentric weight member between a first position and a second position. The movable member includes an offset shaft extending therefrom that defines a second axis. The movable member is movable from the first position to the second position when the rotation of the eccentric weight member is reversed from the first direction to the second direction (and vice versa). The second axis is positioned closer to the first axis when the movable member is in the first position than when the movable member is in the second position.

It will be appreciated that the amplitude variability mechanisms and assemblies discussed herein can be used in any percussive massage device or other power tool where rotating motion is converted to reciprocating motion and an eccentric weight is used. For example, see U.S. Patent Publication No. 2020/0261307 (the "'307 publication") and U.S. patent application Ser. No. 16/824,328 (the "'328 application"), filed Mar. 19, 2020, the entireties of which are incorporated by reference herein. The percussive and/or vibration massage devices taught in the '307 publication and the '328 application include drive trains with motors that include a rotating motor shaft that rotates an eccentric weight and converts the rotating motion of the motor shaft into reciprocating motion of a push rod assembly that is associated with the eccentric weight. The eccentric weight includes a shaft on which is attached a push rod, which is pivotally connected to an output or reciprocating shaft, which includes a massage attachment on the end thereof. The present invention can be utilized in these drive trains to vary the amplitude (ultimately of the massage attachment).

The present invention can also be used in other power tools that include reciprocating motion, such as reciprocating saws and the like.

In a preferred embodiment, the percussive massage device includes the ability to vary the amplitude, thus providing a longer or shorter stroke depending on the application or needs of the user. For example, the device can include a mechanical switch that allows the eccentricity of the connector or moveable member with an offset shaft (or pin structure) to be modified (e.g., between 4 mm and 8 mm). The mechanism can include a push button and a slider. The moveable member (that includes the pin structure) has a spring that lets it fall back into the locked position. The amplitude variability can also be part of the routines or presets taught in the '307 publication. In other words, during the routine, the amplitude can automatically be varied.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
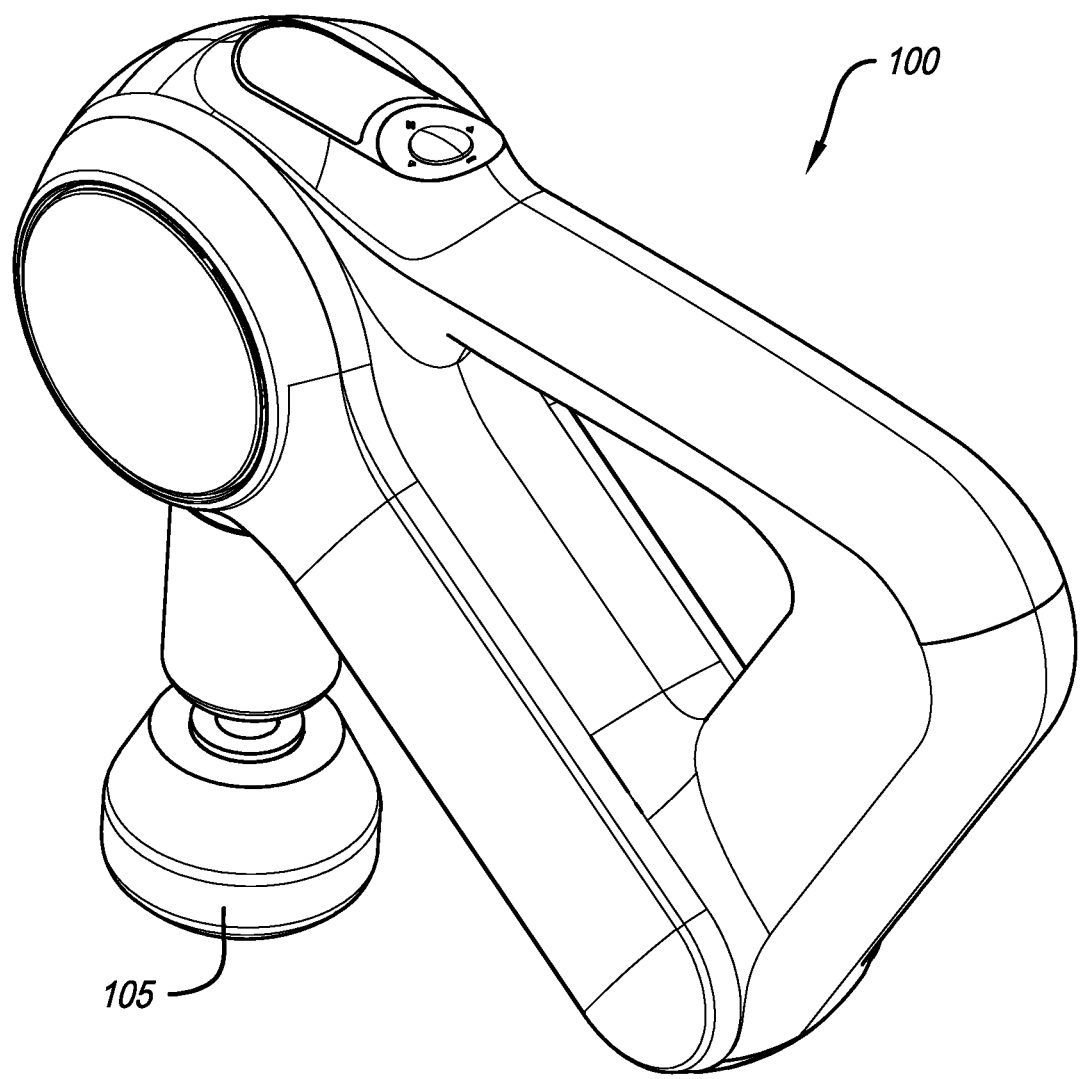
FIG. 1 is a perspective view of a first percussive massage or therapy device that includes a drive train that includes the ability to vary the amplitude in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

Figure 2:
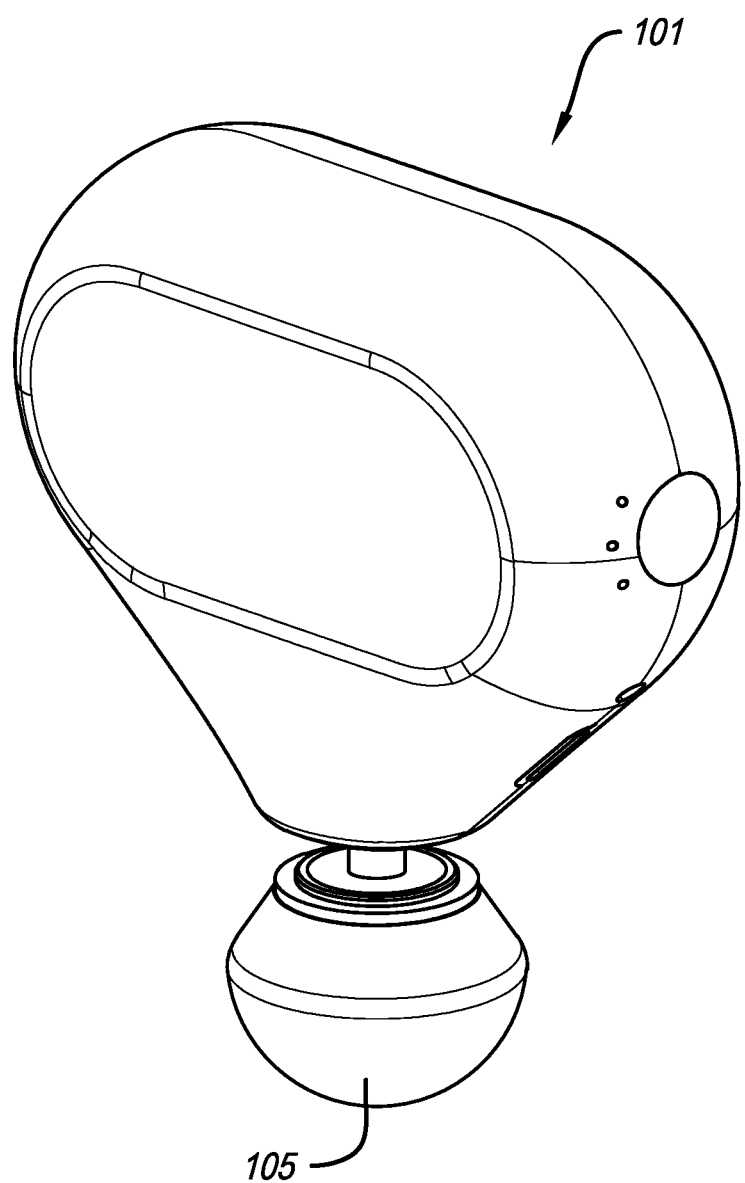
FIG. 2 is a perspective view of a second percussive massage or therapy device that includes a drive train that includes the ability to vary the amplitude.
Figure 3:
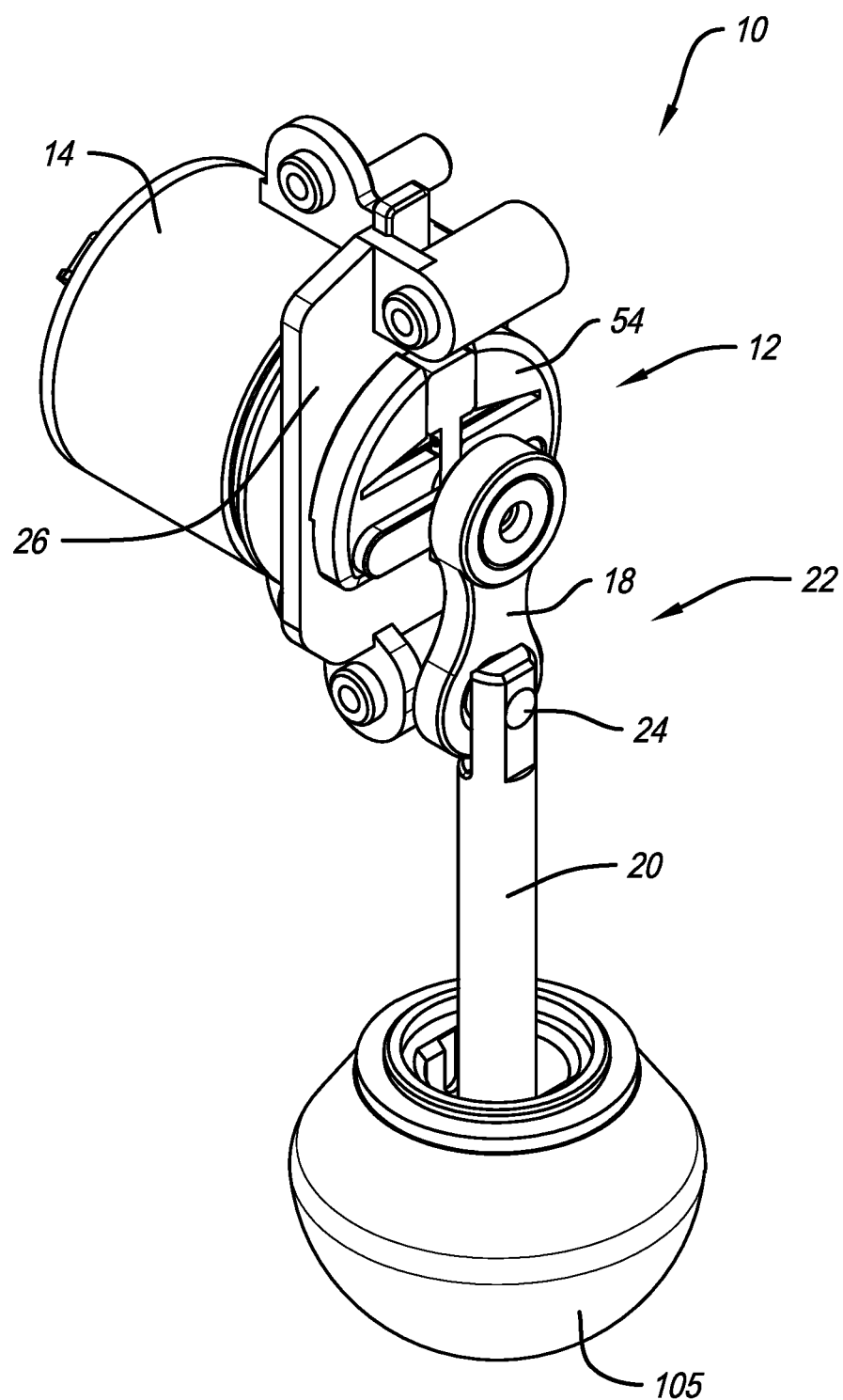
FIG. 3 is a perspective view of a drive train that includes the ability to vary the amplitude in accordance with a preferred embodiment of the present invention.
Figure 4:
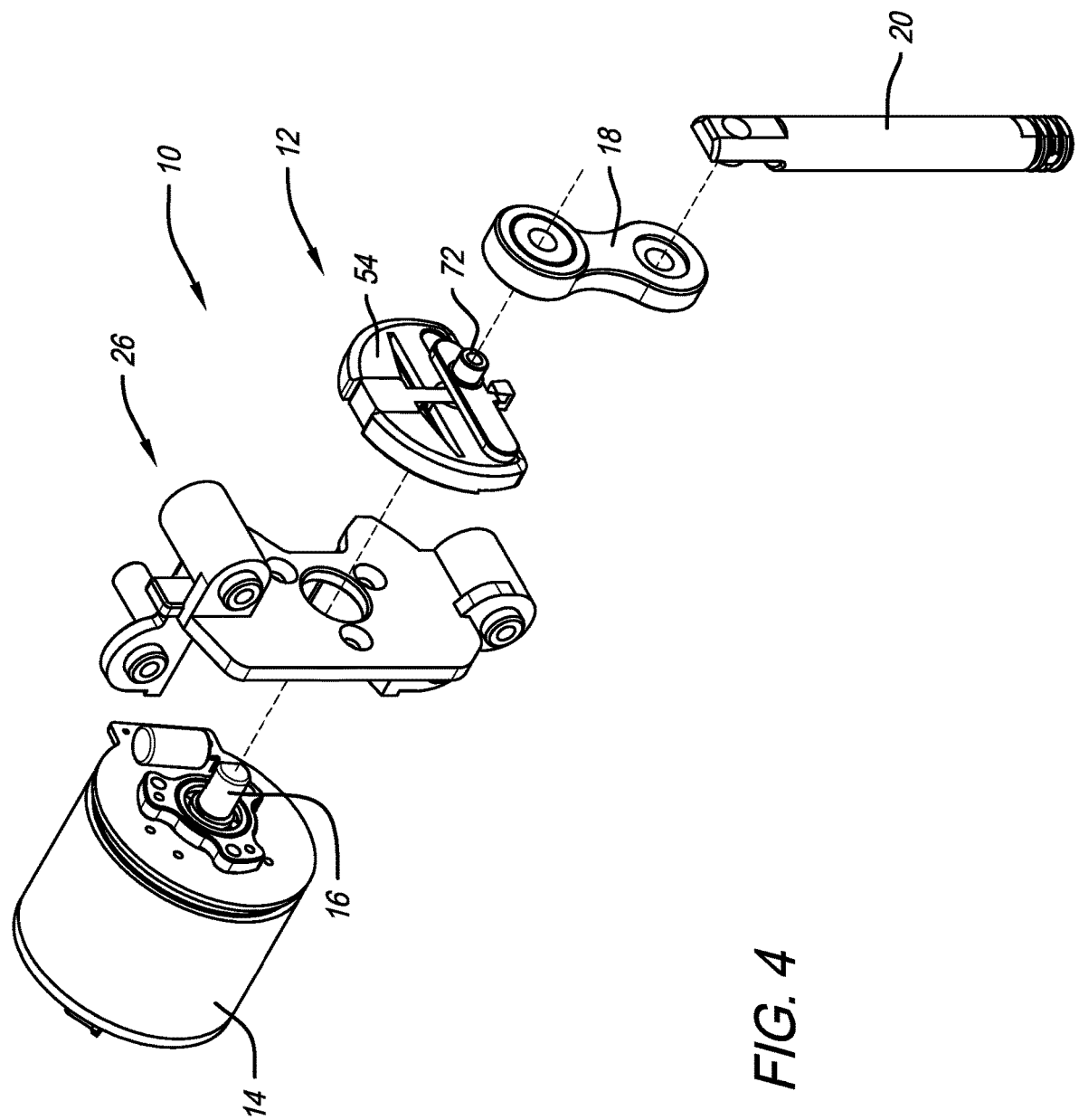
FIG. 4 is an exploded perspective view of the drive train.

Described herein is a system and assembly for varying the amplitude or stroke in percussive massage or therapy devices. Referring now to the drawings, which are for purposes of illustrating the present invention and not for purposes of limiting the same, the drawings show a drive train assembly 10 that includes a variable amplitude assembly 12 that can be used in various percussive massage devices. FIGS. 1 and 2 show different types of percussive massage devices 100 and 101 in which the variable amplitude assembly 12 can be used. The drive train assembly 10 shown in FIG. 3 and other figures is the particular one that can be used in percussive massage device 101.

As shown in FIGS. 3-13, the drive train assembly 10 generally includes the variable amplitude assembly 12, motor 14, motor shaft 16, push rod 18 and reciprocating shaft 20. The rotation of the motor shaft 16 is converted to reciprocating motion of the reciprocating shaft 20 via a linkage assembly (or push rod assembly) 22 that includes the push rod 18 that is pivotably connected to the reciprocating shaft 20 (see pivot pin 24) and a counterweight or an eccentric weight member 54 that is part of the variable amplitude assembly 12. An offset shaft 72 is operatively connected (e.g., pivotably connected) to the push rod 18. It will be appreciated that the axis of the offset shaft 72 is offset from the axis of rotation of the motor shaft 32. In a preferred embodiment, the motor 14 is mounted on a motor mount 26.

Figure 5:
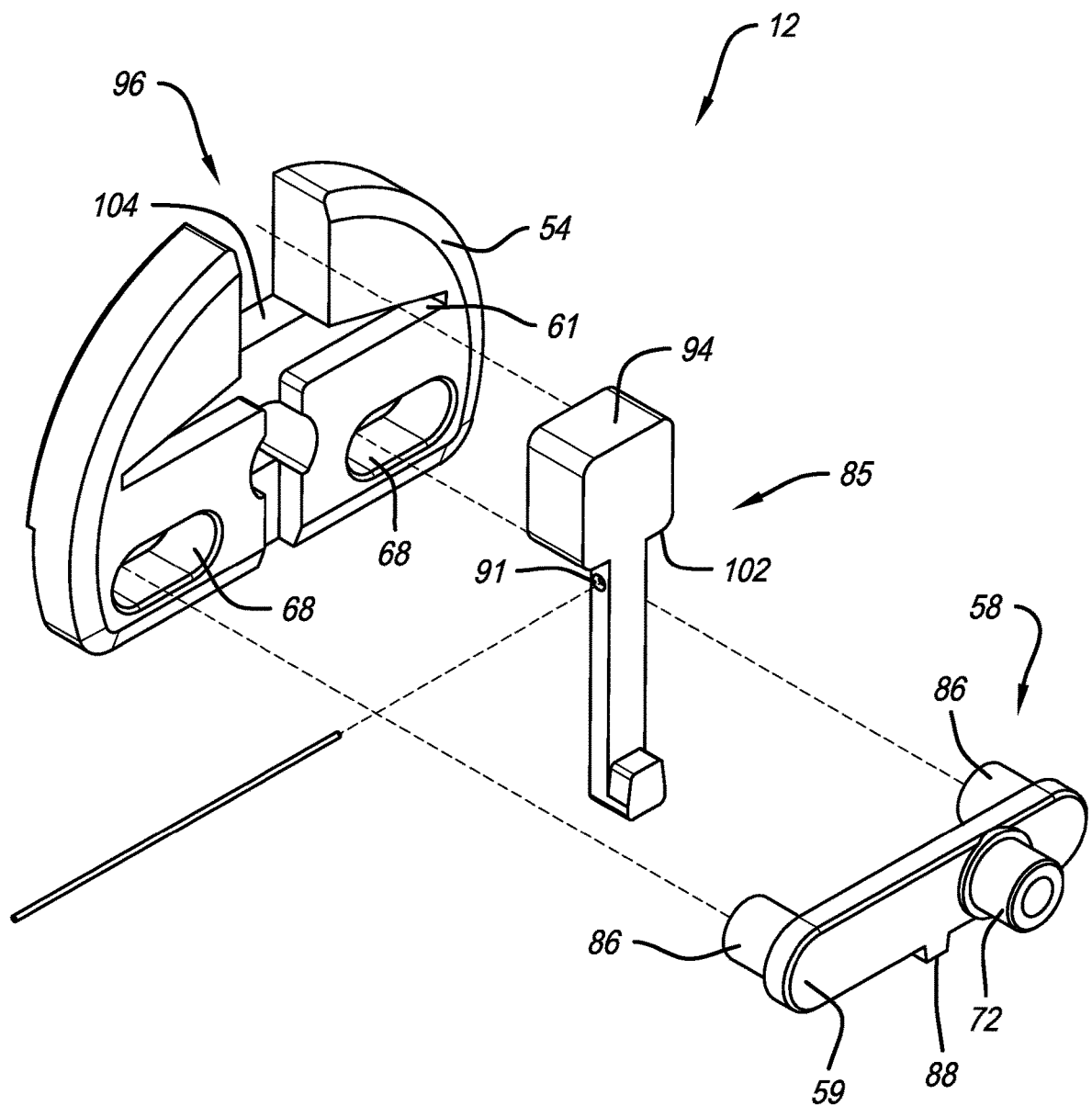
FIG. 5 is an exploded perspective view of a variable amplitude assembly in accordance with a preferred embodiment of the present invention.
Figure 6:
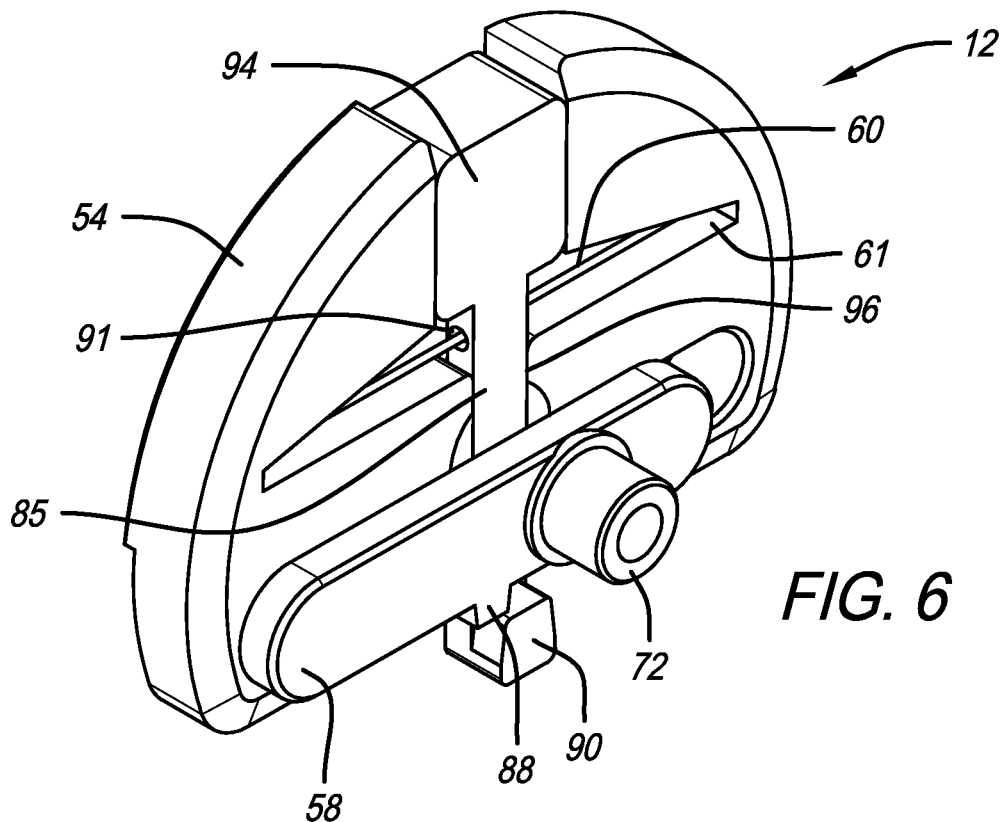
FIG. 6 is a perspective view of the variable amplitude assembly.
Figure 7:
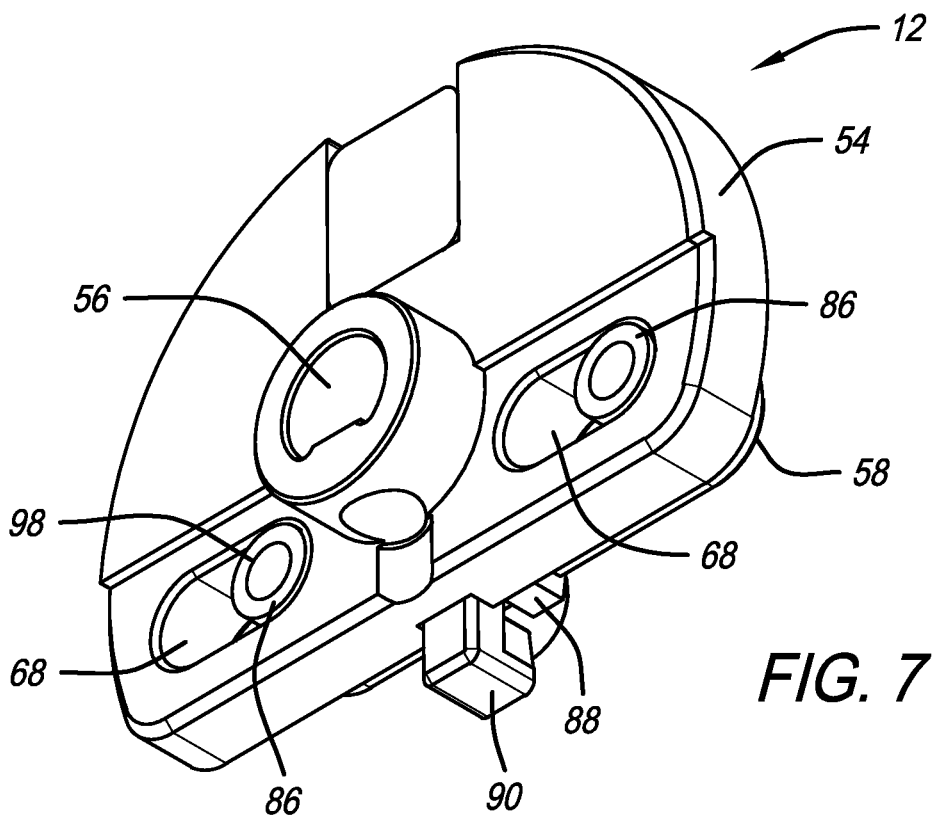
FIG. 7 is a perspective view of the variable amplitude assembly shown from the other side as FIG. 6.

As shown in FIG. 5-7, The variable amplitude assembly 12 includes the eccentric weight member 54 and a shaft opening 56 therein that receives the rotating drive shaft of the motor, an interference member 85, a movable member 58 and a spring 60 (preferably a spring) that is received in a spring channel 61. As shown in FIG. 5, the movable member 58 includes a main body portion 59, two slide members 86 that are received in slots 68 that are defined in the eccentric weight member 54, the offset shaft 72 and a tooth 88 that interacts with a stop member 90 on the interference member 85. The interference member also includes an opening 91 defined therein through which the spring 60 extends, and a weight 94 further described below. The interference member 85 is received in and seated in a channel 96 defined in the eccentric weight member 54. Fasteners (e.g., threaded fasteners) can be received in threaded openings 98 in the slide members 86 to secure the movable member 58 to the eccentric weight member 54. The ends of the spring 60 are received in openings defined in the eccentric weight member that are positioned near the ends of the spring channel 61.

Figure 8:
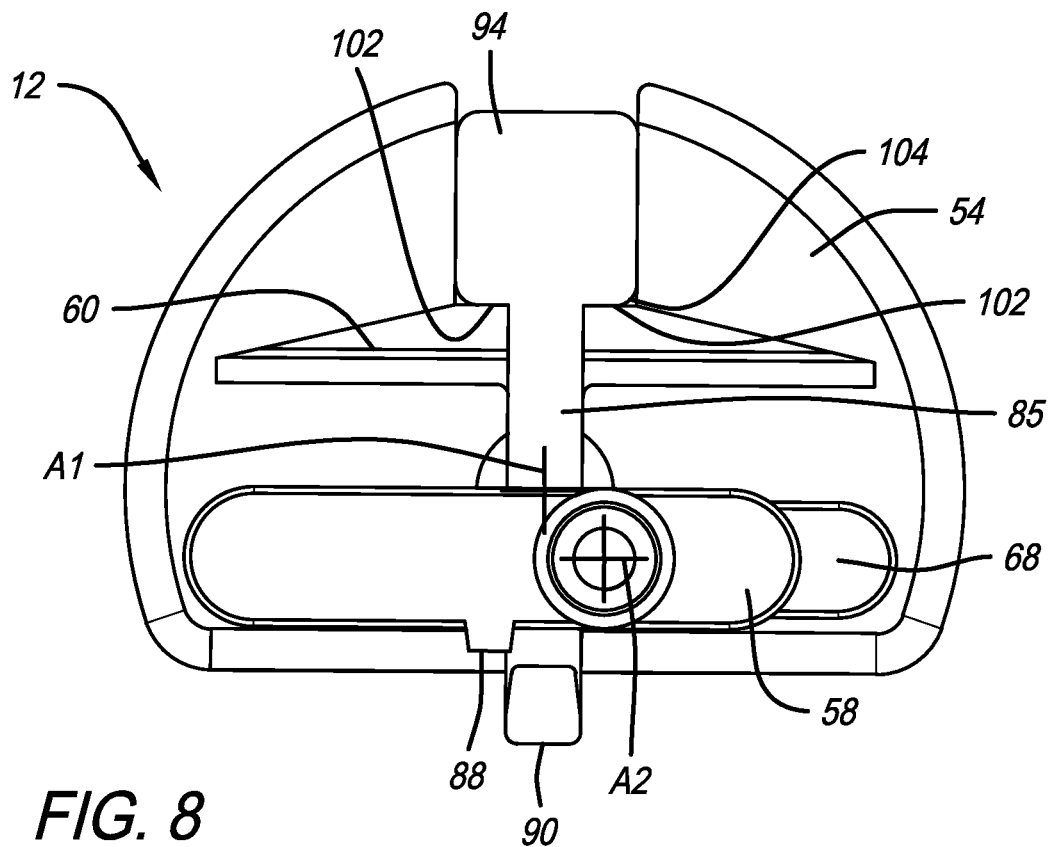
FIG. 8 is an elevational view of the variable amplitude assembly showing the movable member in the first position and the interference member in the rest position.
Figure 9:
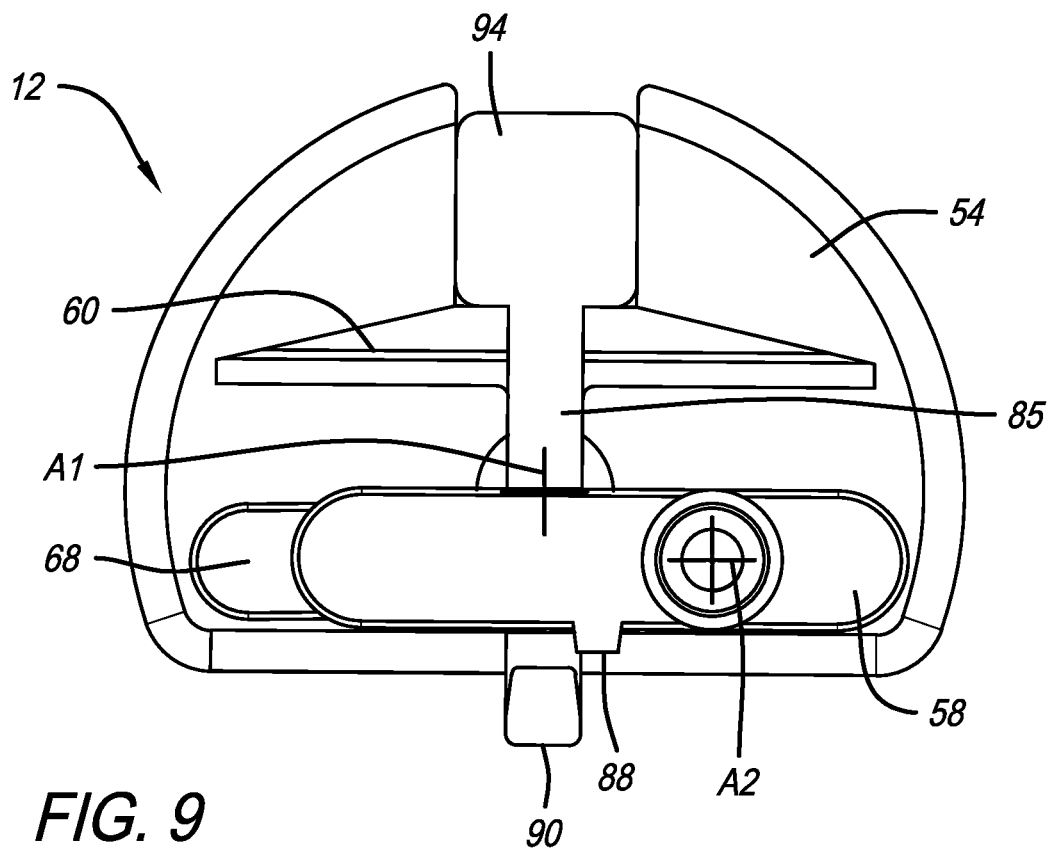
FIG. 9 is an elevational view of the variable amplitude assembly showing the movable member in the second position and the interference member in the rest position.
Figure 10:
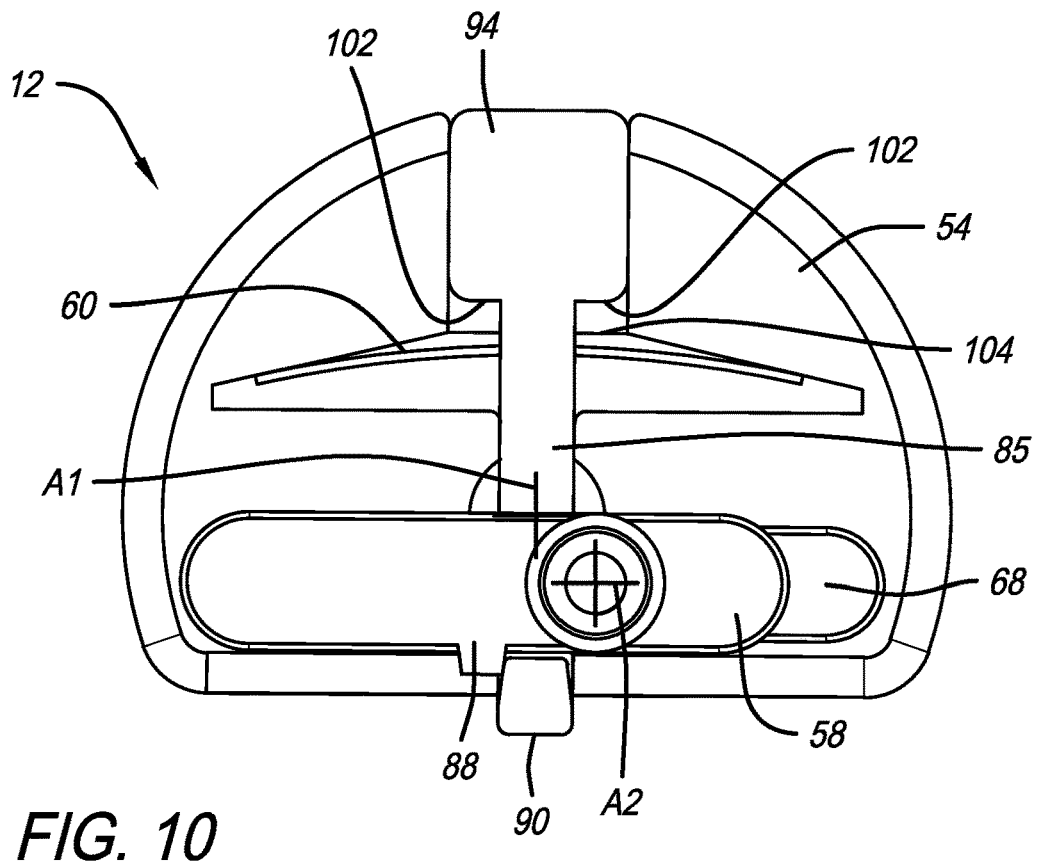
FIG. 10 is an elevational view of the variable amplitude assembly showing the movable member in the first position and the interference member in the deployed position.
Figure 11:
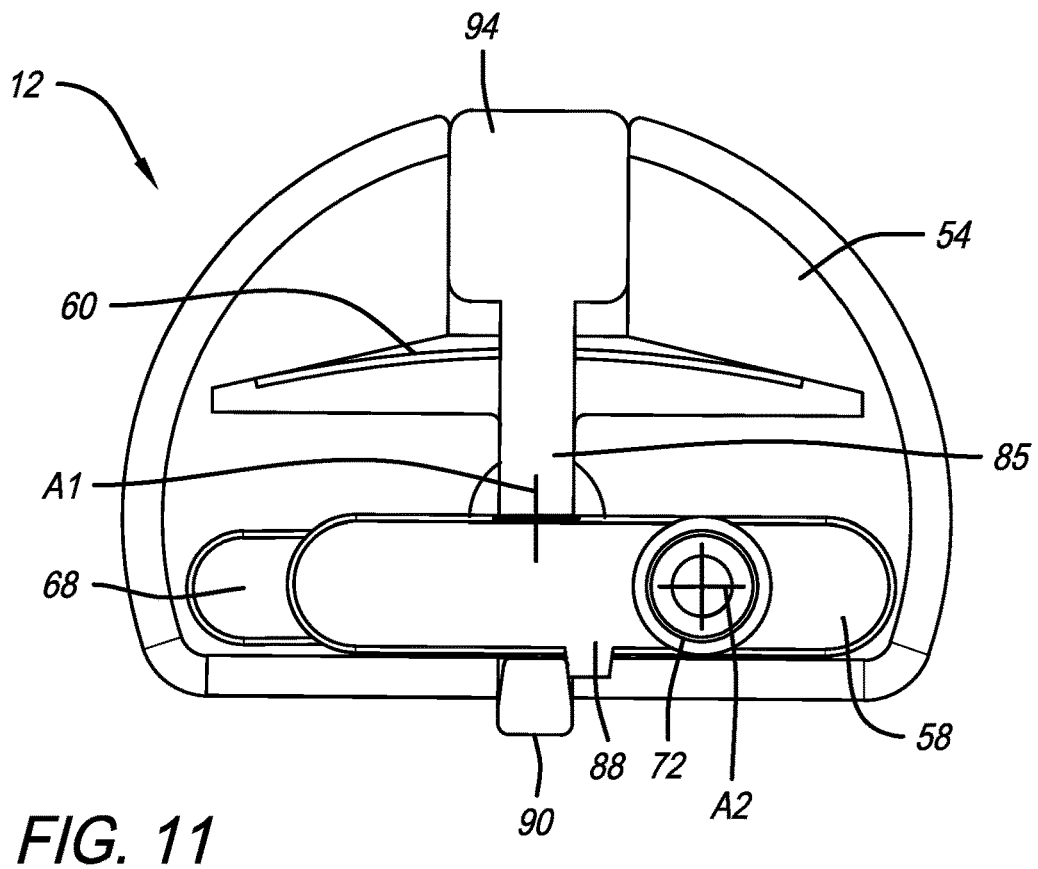
FIG. 11 is an elevational view of the variable amplitude assembly showing the movable member in the second position and the interference member in the deployed position.

FIGS. 8-11 show the different positions of the movable member 58 and the interference member 85. The movable member 58 is movable or slidable between a first position (FIGS. 8 and 10) and a second position (FIGS. 9 and 11). The interference member 85 is movable or slidable between a rest position (FIGS. 8 and 10) and a deployed position (FIGS. 9 and 11). Spring 60 biases the interference member 85 to the rest position. Shoulders 102 on the weight 94 contact stop surface 104 in the rest position (see FIG. 8).

Generally, the movable member 58 is located at the first position when the drive shaft of the motor is rotated in a first direction (clockwise or counterclockwise) and the movable member slides or translates to the second position when the drive shaft is reversed and begins to rotate in the opposite direction. When the motor is at rest and at the beginning of the rotation of the eccentric weight member in either direction, the interference member 85 remains in the rest position. In the rest position, the tooth 88 on the movable member 58 is not in engagement with and is spaced from stop member 90 such that movable member 58 can move linearly along slots 68 (FIGS. 8 and 10). During use, as the eccentric weight member 54 begins to rotate in the opposite direction from the previous use, the eccentric or centripetal force causes the movable member 58 to move to the other of the first or second position. As the eccentric weight member continues to rotate and speed up and reaches a desired RPM, the eccentric or centripetal force on the weight causes the interference member 85 to overcome the spring force of the spring 60 and the interference member 85 moves outwardly within channel 96, thereby causing the stop member 90 to move into the linear path of tooth 88, thus blocking linear movement of the tooth 88 and the movable member 58 and locking or securing the movable member FIGS. 9 and 11) in either the first or second position (depending on the rotational direction of the eccentric weight member 54).

Eccentric force causes the movable member 58 and the slide members 86 to move to the opposite end of the slots 68 when the motor is reversed. It will be appreciated that the movable member 58 will be located at the first position, as shown in FIGS. 8 and 10, when the eccentric weight member 54 is rotated counterclockwise (based on the configuration shown in FIGS. 8-11) and the movable member 58 will be located at the second position, as shown in FIGS. 9 and 11, when the eccentric weight member 54 is rotated clockwise (based on the configuration shown in FIGS. 8-11). Essentially, the opposite ends of slots 68 are stop members that stop the movable member 58 as it moves when the motor direction is reversed. In short, the direction of rotation of the motor drive shaft determines the amplitude of the reciprocating movement of the reciprocating shaft and, therefore, the massage attachment.

FIGS. 8 and 9 also show the axis of rotation A1 of the eccentric weight member 54 and the axis of offset shaft 72 A2. As can be seen in a comparison of FIG. 8 to FIG. 9, the distance between A1 and A2 is greater when the movable member 58 is in the second position than when the movable member 58 is in the first position. As a result, the reciprocating shaft 20 (and massage attachment 105) has a greater amplitude or stroke when the movable member 58 is in the second position than when the movable member 58 is in the first position. In an exemplary embodiment, the amplitude is 8 mm when the movable member is in the first position (A1 is 4 mm from A2) and 16 mm when the movable member is in the second position (A1 is 8 mm from A2). These numbers are only exemplary and the range can be wider or small than discussed above. In a preferred embodiment, shaft 72 (and A2) are positioned closer to one end of movable member 58 than the other to provide the different distances between A1 and A2 when the movable member is in the first and second positions. It will be appreciated that the drive train 50 can be used with any type of motor. The use of a brushless DC motor is not limiting on the invention.

Figure 12:
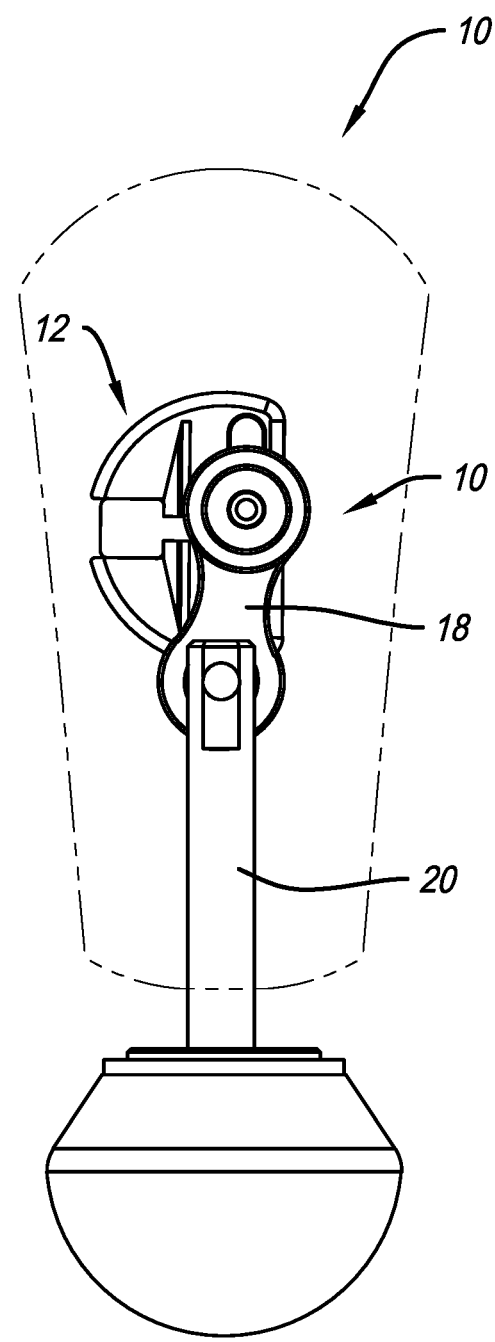
FIG. 12 is a side elevational view of the drive train in the second percussive therapy device and with the moveable member in the first position, thus providing a smaller amplitude.
Figure 13:
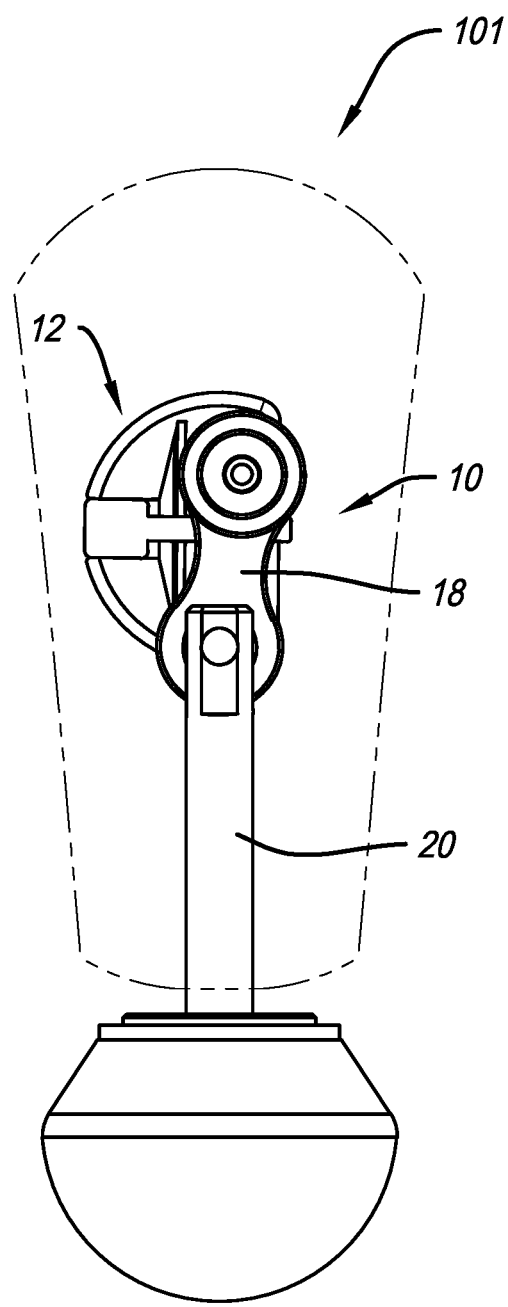
FIG. 13 is a side elevational view of the drive train in the second percussive therapy device and with the moveable member in the second position, thus providing a larger amplitude.

FIGS. 12 and 13 show the variable amplitude mechanism or assembly 12 in the drive train 10 of percussive massage device 101. FIG. 12 shows the variable amplitude assembly 12 with the movable member in the first position and FIG. 13 shows the variable amplitude assembly 12 with the movable member in the second position.

Figure 14:
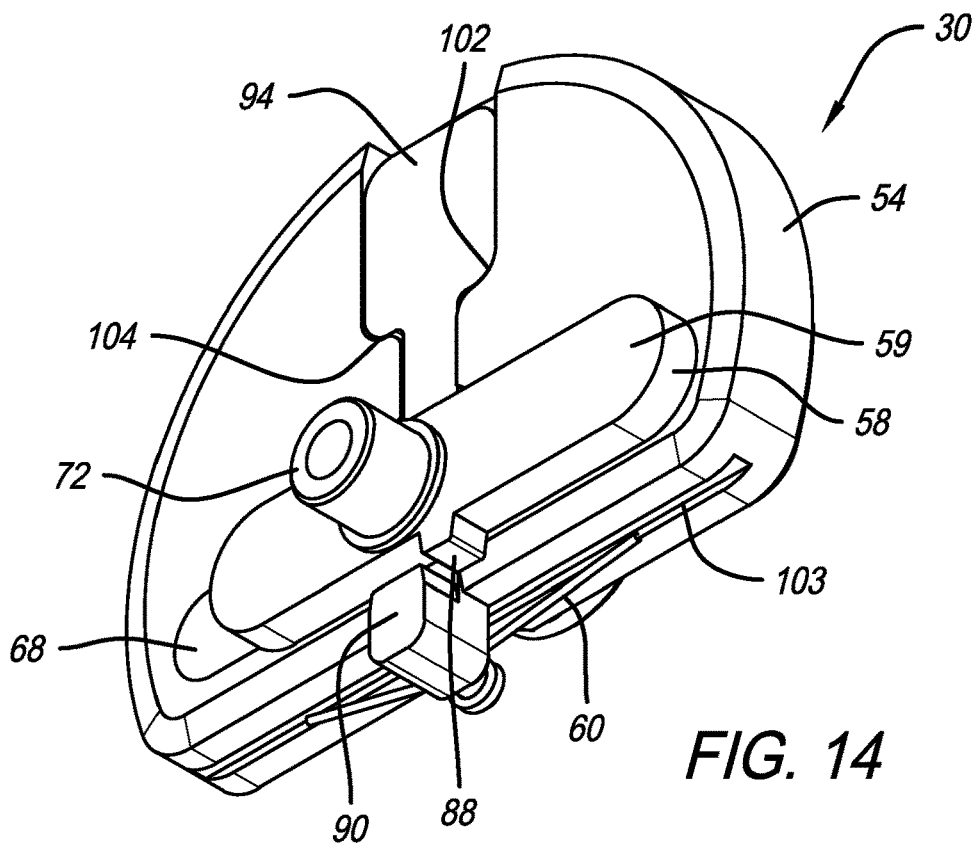
FIG. 14 is a perspective view of a variable amplitude assembly in accordance with a preferred embodiment of the present invention.

FIG. 14 shows another preferred embodiment of a variable amplitude assembly 30 that is a variation of the variable amplitude assembly 12 shown in FIGS. 3-13. Therefore, all text above related to the previous embodiment applies to this embodiment as well and all parts are interchangeable.

As shown in FIG. 14, variable amplitude assembly 30 includes the eccentric weight member 54, interference member 85, movable member 58 and spring 60 (preferably a torsion spring) that is received on a pin 92 that is part of and/or extends from the interference member 85. The movable member 58 includes shaft 72 that receives and, in use, reciprocates push rod 62 and tooth 88 that interacts with stop member 90 on the interference member 85. The interference member also includes a pin 92 that receives the coil portion of the spring 60 and a weight 94 further described below. The interference member 85 is received in and seated in channel 96 defined in the eccentric weight member 54. As shown in FIG. 14, the ends of the torsion spring 60 are received in and movable along a linear groove 103 defined in a side surface of the eccentric weight member 54. The positioning of the spring 60 is the biggest difference with the embodiment above. However, the spring 60 operates in the same manner as the spring in the embodiment shown FIGS. 3-13. Spring 60 biases the interference member 85 to the rest position. Shaft opening 56, and slide members 86 are not shown in FIG. 14, but are the same as shown in FIG. 7. The positioning of the movable member 58, offset shaft 72, interference member 85, axes A1 and A2 and related components shown in FIGS. 8-11 apply to variable amplitude assembly 30.

During use of variable amplitude assembly 30, as the eccentric weight member 54 begins to rotate in the opposite direction from the previous use, the eccentric or centripetal force causes the movable member 58 to move to the other of the first or second position. As the eccentric weight member continues to rotate and speed up and reaches a desired RPM, the eccentric or centripetal force on the weight causes the interference member 85 to overcome the spring force of the spring 60 and the interference member 85 moves outwardly within channel 96, thereby causing the stop member 90 to move into the linear path of tooth 88, thus blocking linear movement of the tooth 88 and the movable member 58 and locking or securing the movable member FIGS. 9 and 11) in either the first or second position (depending on the rotational direction of the eccentric weight member 54).

FIGS. 15-20 show another embodiment of a variable amplitude assembly 110 for use with a drive train in a percussive massage device for varying the amplitude of the output shaft and the massage element or attachment. Variable amplitude assembly 110 operates similarly to variable amplitude assemblies 12 and 30 above, but uses an electromagnet instead of the eccentric force to move the interference member 85. Therefore, all text herein related to the other embodiments discussed applies to this embodiment as well and all parts are interchangeable.

Figure 15:
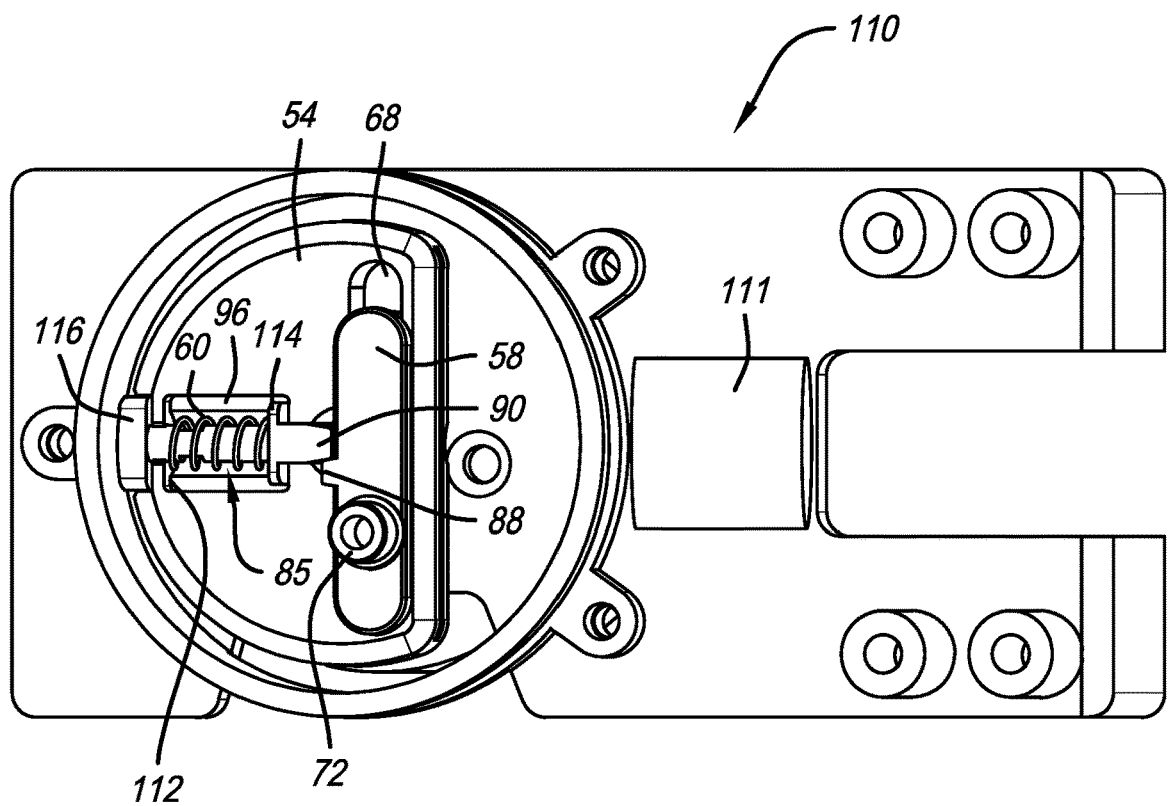
FIG. 15 is a perspective view of a variable amplitude assembly that includes an electromagnet in accordance with a preferred embodiment of the present invention.
Figure 16:
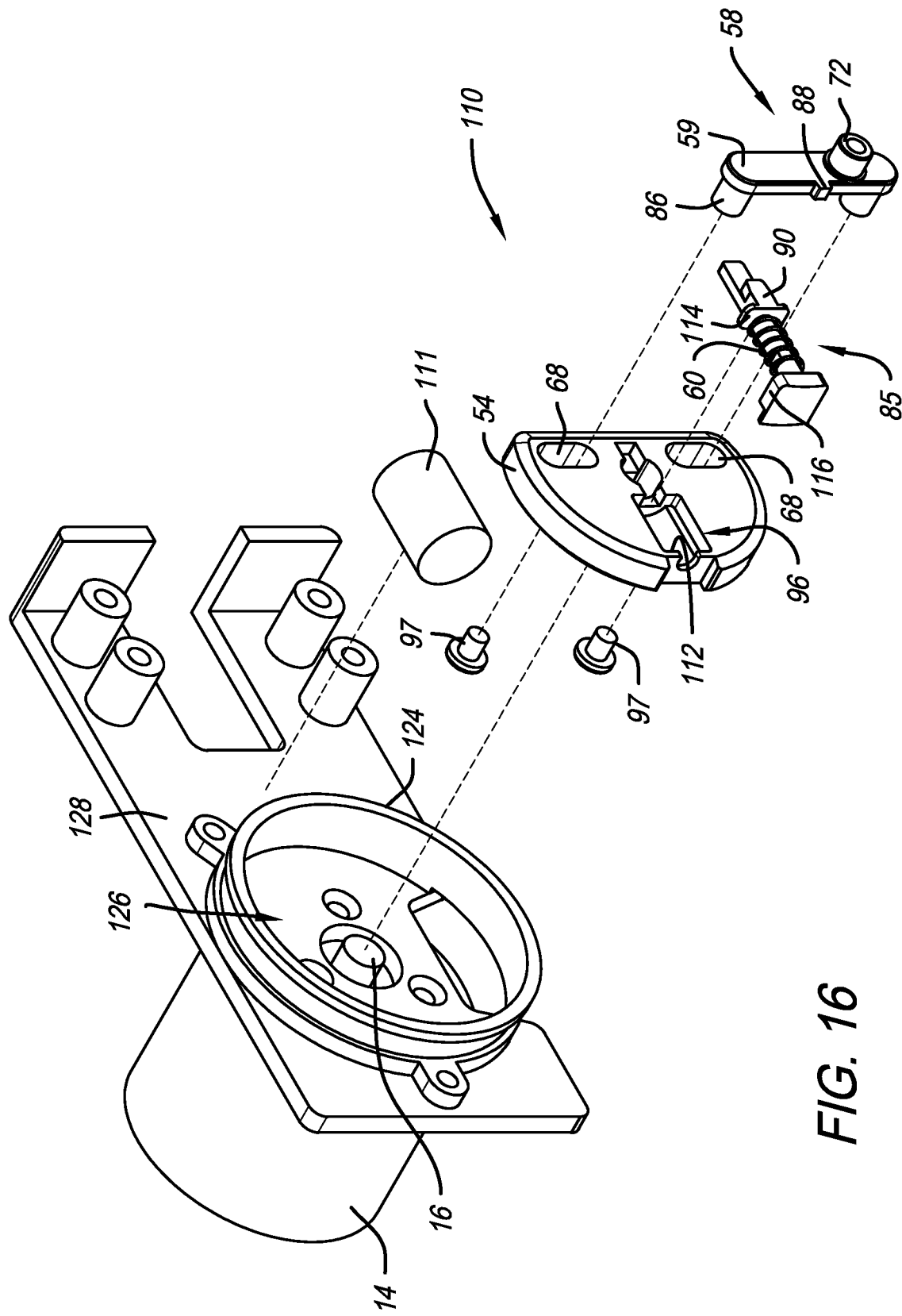
FIG. 16 is an exploded perspective view of the variable amplitude assembly of FIG. 15.

As shown in FIGS. 15-16, The variable amplitude assembly 110 includes eccentric weight member 54 and a shaft opening (not shown) therein that receives the rotating drive shaft 16 of the motor 14, an interference member 85, a movable member 58, and a spring 60 (preferably a coil spring). As shown in FIG. 16, the movable member 58 includes one or more slide members 86 that are received in slots 68 that are defined in the eccentric weight member 54, an offset shaft 72 that receives and, in use, reciprocates the push rod and a tooth 88 that interacts with a stop member 90 on the interference member 85. The interference member 85 is received in and extends through a channel 96 defined in the eccentric weight member 54. The spring 60 is received on a shaft portion of interference member 85 and extends between a first end 112 of channel 96 and an extension member 114 on the interference member 85. The interference member 85 includes a head portion 116. Threaded fastener(s) 97 are receive in threaded openings in the slide member(s) 86 and secure the movable member 58 to the eccentric weight member 54.

As shown in FIGS. 15 and 16, the variable amplitude assembly 110 includes an electromagnet 111. The electromagnet 111 is positioned outside a cylinder 124 on a mounting bracket 128. The cylinder 124 defines a rotation space 126 for the eccentric weight member 54. The electromagnet 111 is also positioned adjacent or close enough to head portion 116 of the interference member 85 that the electromagnet can pull the interference member radially outwardly and toward the electromagnet 111 when it is energized or turned on. Space is defined between the outer surface of the eccentric weight member 54 and the inner surface of the cylinder 124. This allows space for the head portion 116 (which is made of metal) to move outwardly and out of the head space defined in the eccentric weight member 54 in which it is seated. When the head portion 116 and the remainder of the interference member 85 is moved outwardly, the movable member 58 can move linearly, as described below.

Figure 17:
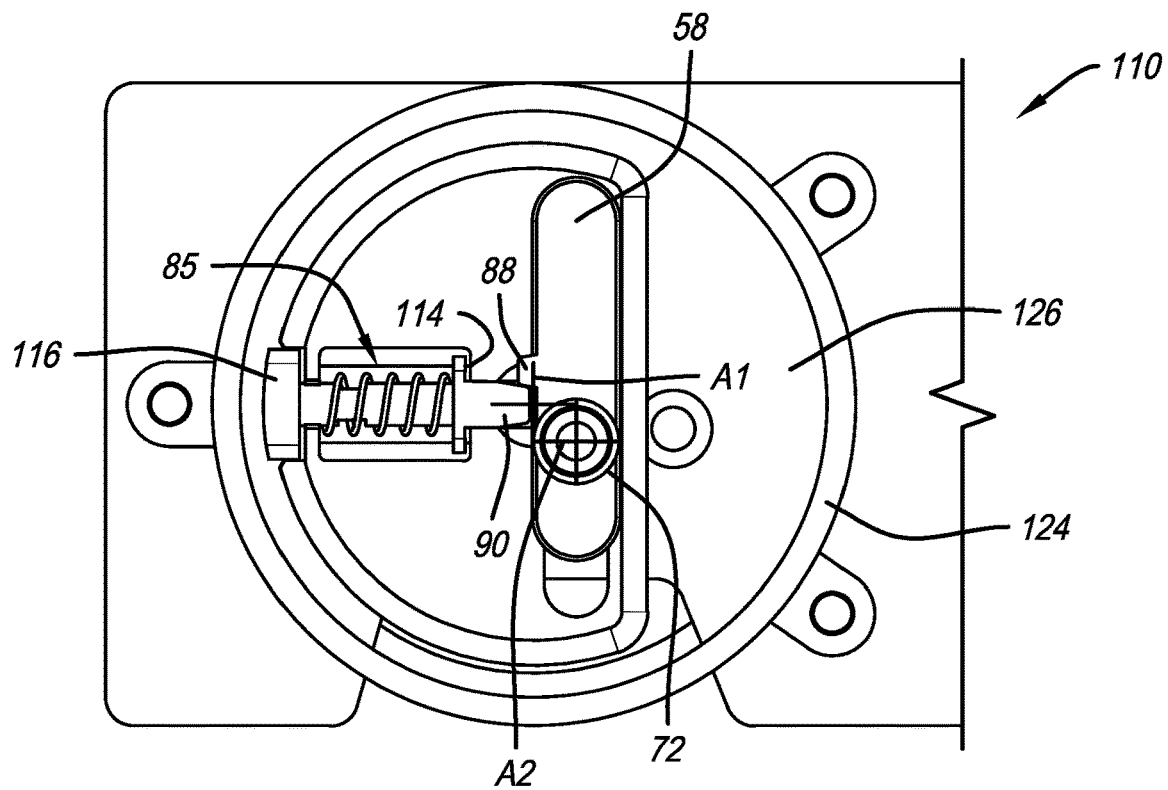
FIG. 17 is an elevational view of the variable amplitude assembly showing the movable member in the first position and the interference member in the rest position.
Figure 18:
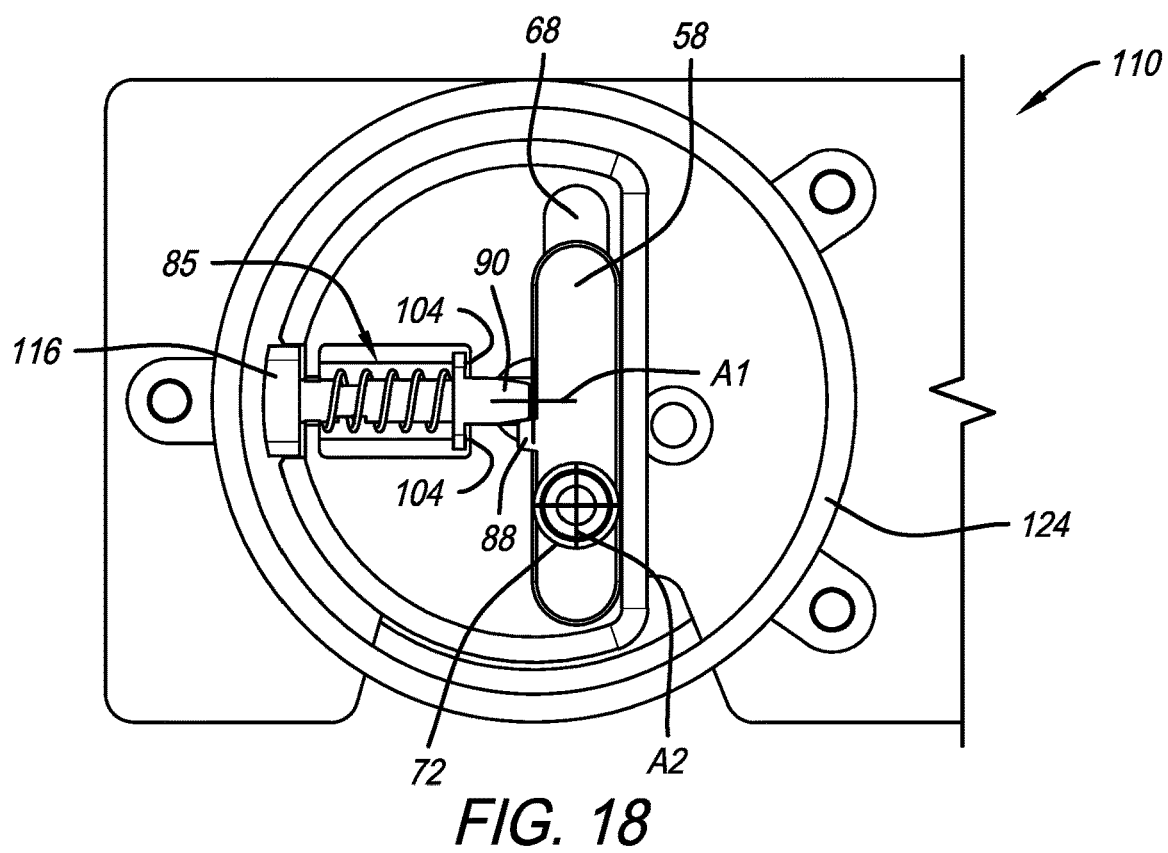
FIG. 18 is an elevational view of the variable amplitude assembly showing the movable member in the second position and the interference member in the rest position.
Figure 19:
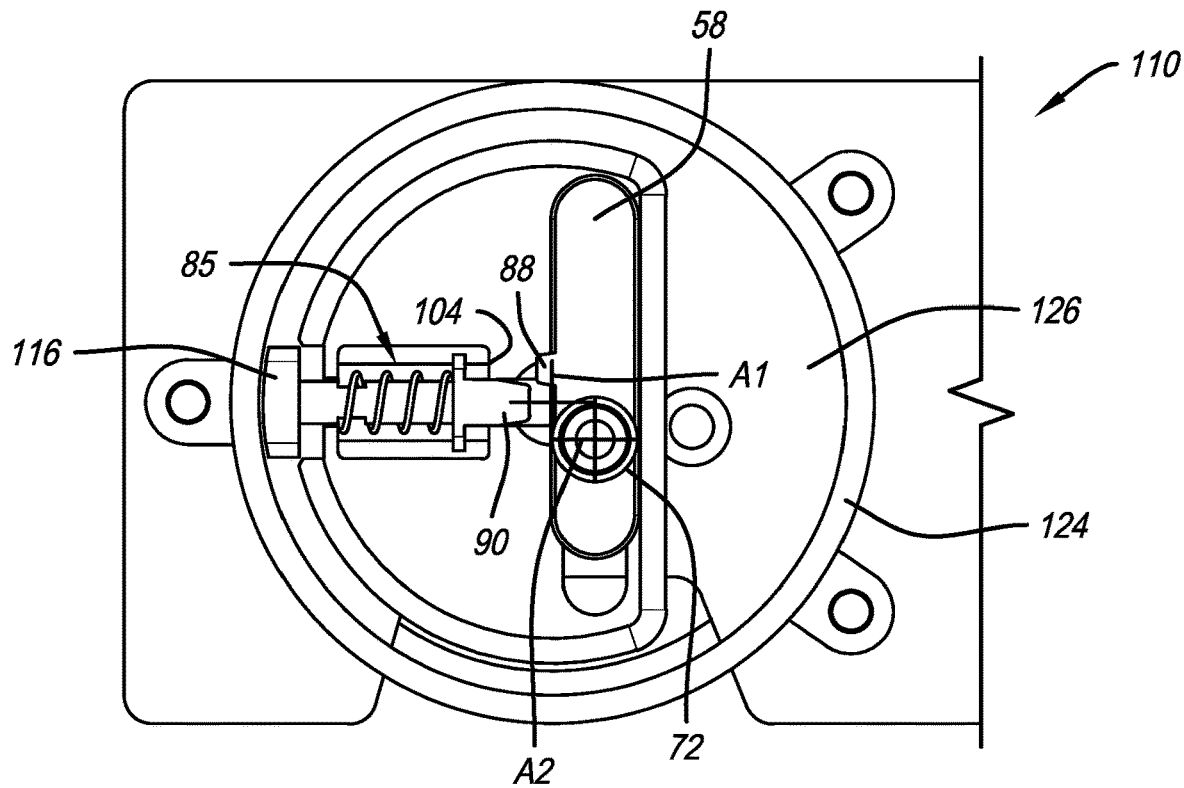
FIG. 19 is an elevational view of the variable amplitude assembly showing the movable member in the first position and the interference member in the deployed position.
Figure 20:
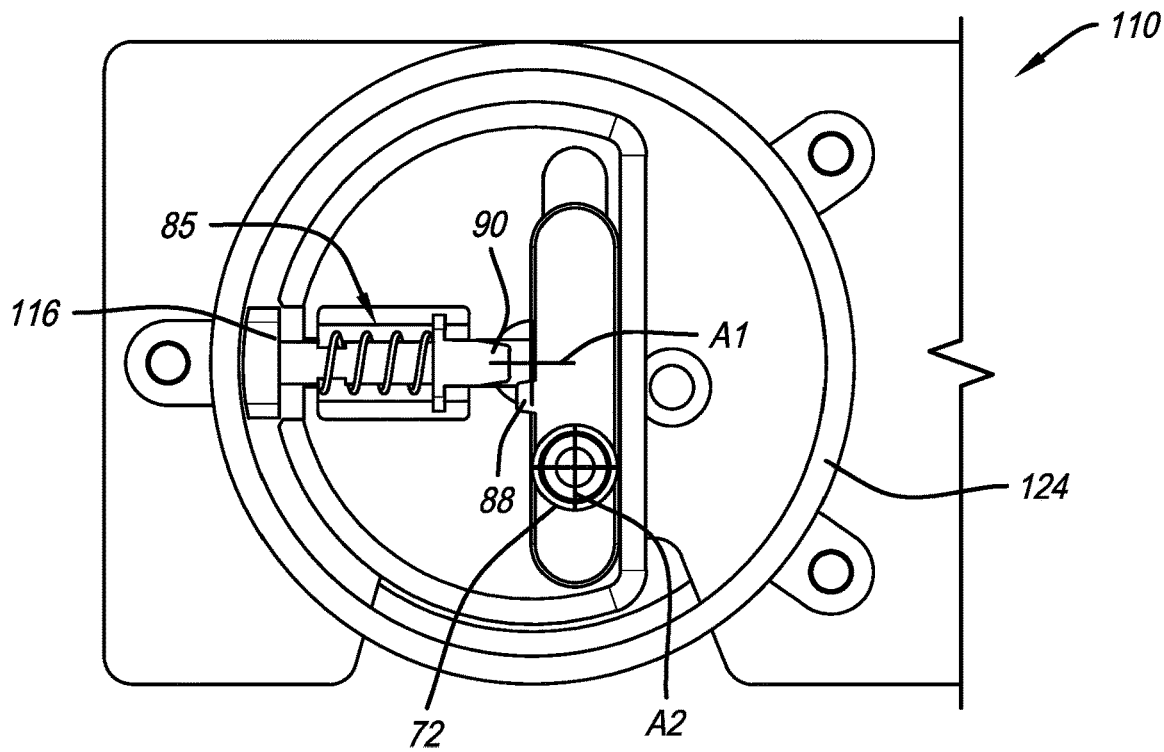
FIG. 20 is a side elevational view of the variable amplitude assembly showing the movable member in the second position and the interference member in the deployed position.

FIGS. 17-20 show the different positions of the movable member 58 and the interference member 85. The movable member 58 is movable or slidable between a first position (FIGS. 17 and 19) and a second position (FIGS. 18 and 20). The interference member 85 is movable or slidable between a rest position (FIGS. 17 and 18) and a deployed position (FIGS. 19 and 20). Spring 60 biases the interference member 85 to the rest position. The extension member(s) 114 contact stop surfaces 104 in the rest position (see FIG. 18).

Generally, the movable member 58 is located at the first position when the drive shaft of the motor is rotated in a first direction (clockwise or counterclockwise) and the movable member slides or translates to the second position when the drive shaft is reversed and begins to rotate in the opposite direction. When the motor 122 is at rest and at the beginning of the rotation of the eccentric weight member in either direction, the interference member 85 remains in the rest position. In the rest position, the tooth 88 on the movable member 58 engages with stop member 90 such that movable member 58 cannot move linearly along slots 68 (FIGS. 17 and 18). During use, when the amplitude is to be changed, the eccentric weight member 54 begins to rotate in the opposite direction from the previous use and the electromagnet 111 is energized, thereby attracting the head portion 116 of the interference member 85 to the deployed position and pulling the stop member 90 away from the movable member and tooth 88, such that stop member 90 is no longer in the linear path of tooth 88 (the tooth path between the first position and the second position) (see FIGS. 19 and 20). As a result, the eccentric or centripetal force causes the movable member 58 to move to the other of the first or second position (from the position in FIG. 25 to the position in FIG. 26 or vice versa). Once this happens or after a predetermined time or when the motor reaches a predetermined RPM, electromagnet 111 is turned off or deenergized and the spring biases the interference member 85 back to the rest position, thereby causing the stop member 90 to move into the linear path of tooth 88 and locking or securing the movable member in either the first or second position (depending on the rotational direction of the eccentric weight member 54).

Figure 24:
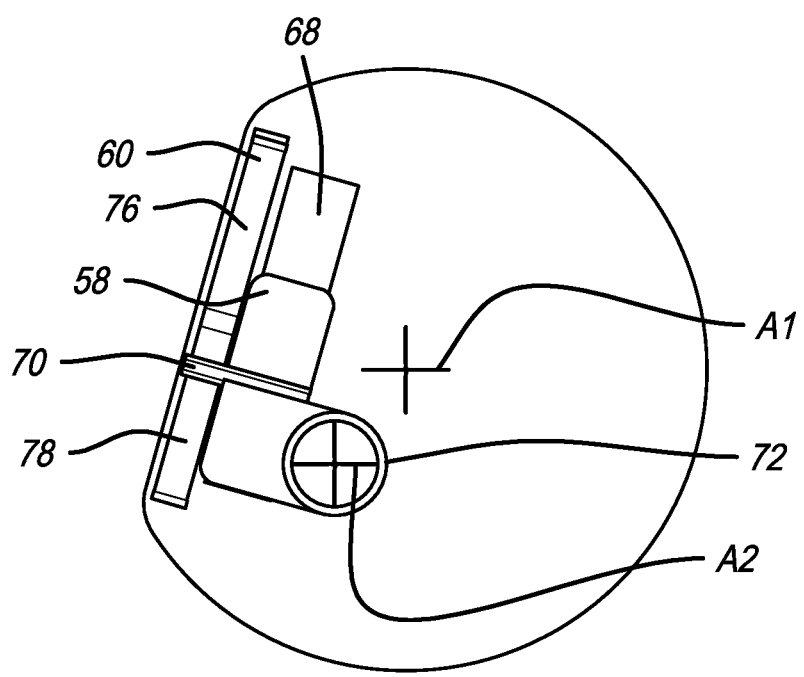
FIG. 24 is an elevational view of the variable amplitude assembly showing the movable member in the second position.

Eccentric force causes the movable member 58 and the slide members 86 to move to the opposite end of the slots 68 when the motor is reversed (and the tooth 88 and stop member 90 are not engaged). It will be appreciated that the movable member 58 will be located at the first position, as shown in FIGS. 17 and 19, when the eccentric weight member 54 is rotated counterclockwise (based on the configuration shown in FIGS. 17-20) and the movable member 58 will be located at the second position, as shown in FIGS. 24 and 26, when the eccentric weight member 54 is rotated clockwise (based on the configuration shown in FIGS. 17-20). Essentially, the opposite ends of slots 68 are stop members that stop the movable member 58 as it moves when the motor direction is reversed. In short, the direction of rotation of the motor drive shaft determines the amplitude of the reciprocating movement of the reciprocating shaft and, therefore, the massage attachment.

FIGS. 17 and 18 also show the axis of rotation A1 of the eccentric weight member 54 and the axis of shaft 72 A2. As can be seen in a comparison of FIG. 17 to FIG. 18, the distance between A1 and A2 is greater when the movable member 58 is in the second position than when the movable member 58 is in the first position. As a result, the reciprocating shaft 20 (and massage attachment 105) have a greater amplitude or stroke when the movable member 58 is in the second position than when the movable member 58 is in the first position. In an exemplary embodiment, the amplitude is 8 mm when the movable member is in the first position (A1 is 4 mm from A2) and 16 mm when the movable member is in the second position (A1 is 8 mm from A2). These numbers are only exemplary and the range can be wider or small than discussed above. In a preferred embodiment, shaft 72 (and A2) are positioned closer to one end of movable member 58 than the other to provide the different distances between A1 and A2 when the movable member is in the first and second positions. It will be appreciated that the drive train can be used with any type of motor. The use of a brushless DC motor is not limiting on the invention.

FIGS. 21-24 show another embodiment of a variable amplitude assembly 52 for use with a drive train in a percussive massage device for varying the amplitude of the output shaft and the massage element or attachment. Variable amplitude assembly 52 operates similarly to other variable amplitude assemblies discussed herein, but uses a leaf spring 60. Therefore, all text herein related to the other embodiments discussed applies to this embodiment as well and all parts are interchangeable.

Figure 21:
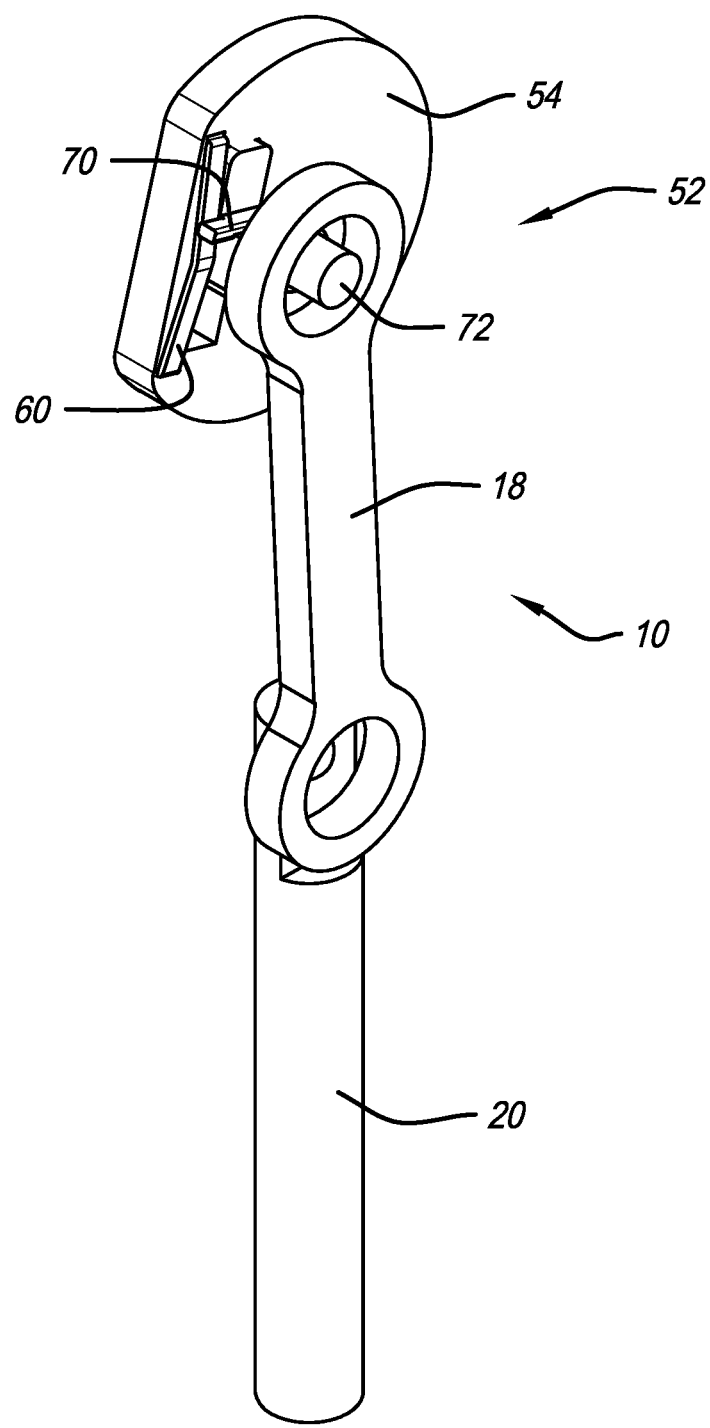
FIG. 21 is a perspective view of a drive train that includes a variable amplitude assembly in accordance with a preferred embodiment of the present invention.
Figure 22:
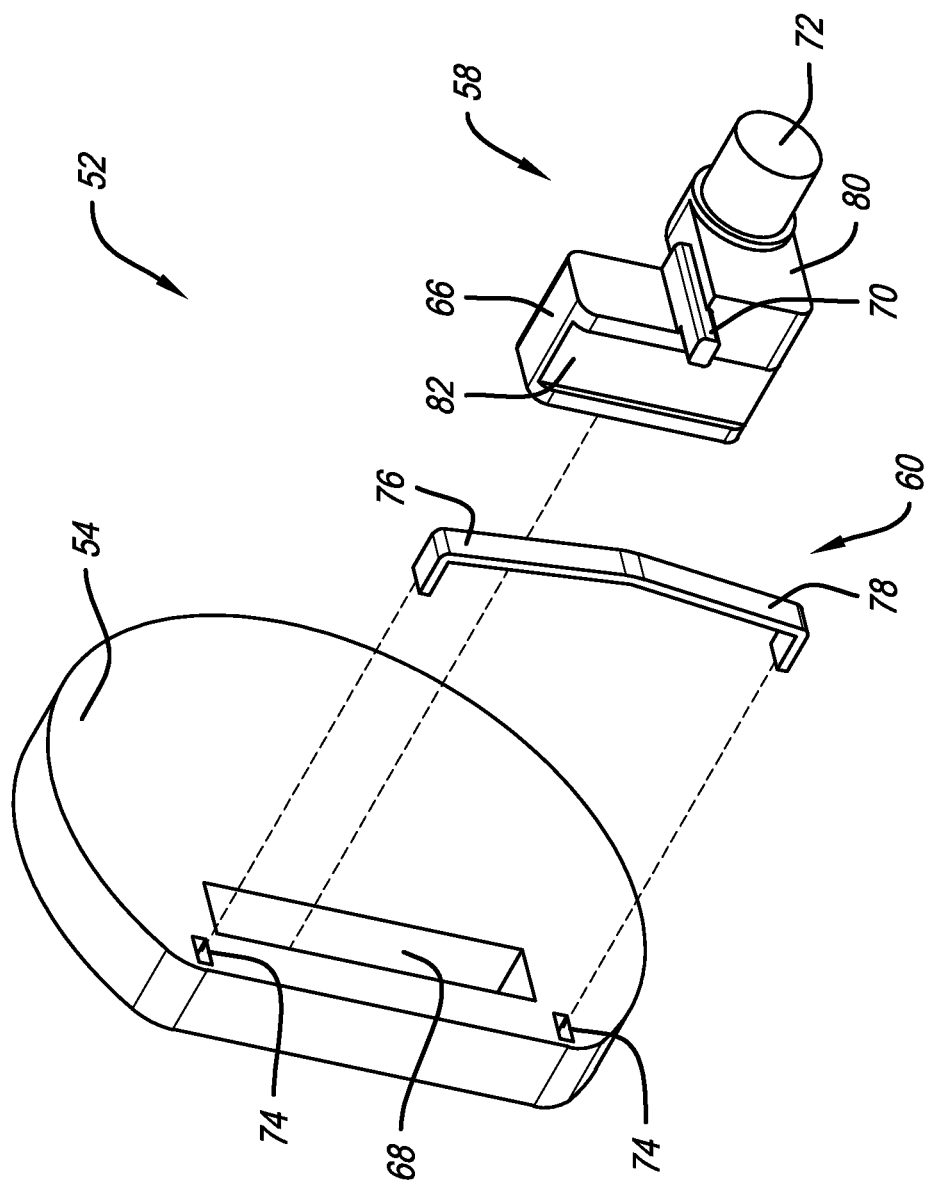
FIG. 22 is an exploded perspective view of the variable amplitude assembly.

As shown in FIGS. 21-22, the variable amplitude assembly 52 includes a eccentric weight member 54, a movable member 58, spring 60 and slot 68. The movable member 58 includes a slide portion 66 that is received in slot 68 that is defined in the eccentric weight member 54, a pin 70 that extends outwardly and contacts spring 60 and an offset shaft 72 that receives and, in use, reciprocates the push rod 18. It will be appreciated that the connections between the push rod 18 and the shaft 72 and the push rod 18 and the reciprocating shaft 20 are not shown in the drawings.

As shown in FIG. 22, the eccentric weight member 54 includes recesses 74 defined therein that receive opposite ends of the spring 60. In a preferred embodiment, the spring 60 is a leaf spring and has a central portion that is spaced from the eccentric weight member 54. The central portion includes a first position portion 76 and a second position portion 78 that meet at an apex. The pin 70 extends outwardly and contacts the first position portion 76 when the movable member 58 is in the first portion and the second position portion 78 when the movable member 58 is in the second portion. The spring 60 is biased away from the eccentric weight member and against the pin 70. As a result, the spring 60 helps hold the movable member 58 in the proper position and also helps prevent rattling and noise. When the rotation of the eccentric weight member 54 is reversed, the eccentric force is enough to overcome the spring force of the spring 60 to allow the movable member 58 to move along slot 68 to the opposite end and for the pin 70 to travel over the apex of the spring 60 and to the other of the first or second position portion.

As shown in FIG. 22, the movable member 58 includes a main body portion 80, the pin 70, the slide portion 66 and shaft 72. In a preferred embodiment, the slide portion 66 also includes channels 82 that engage or slide on the inner surfaces of the long sides of slot 68.

Figure 23:
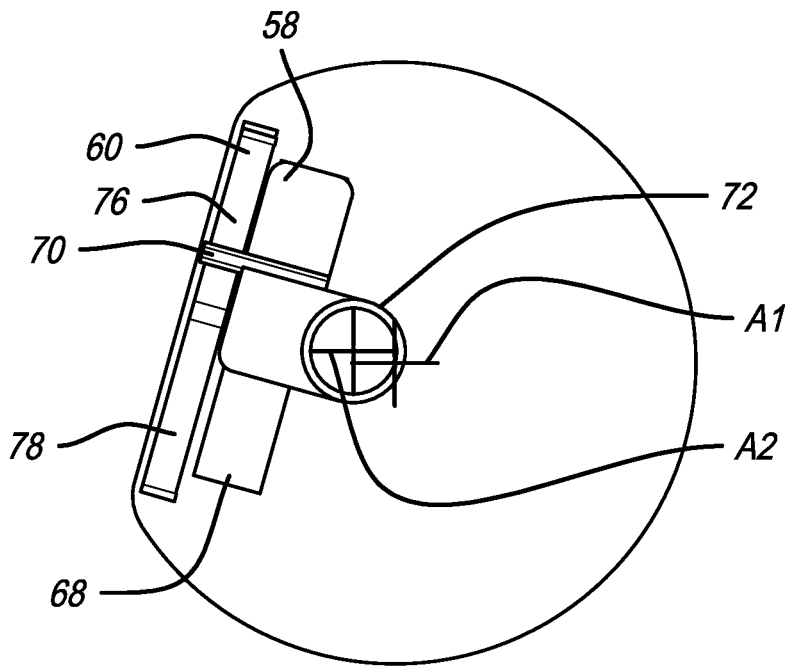
FIG. 23 is an elevational view of the variable amplitude assembly showing the movable member in the first position.

As shown in FIGS. 23 and 24, the movable member 58 is positionable or movable within slot 68 between a first position (FIG. 23) and a second position (FIG. 24). Generally, the movable member 58 is located at the first position when the drive shaft of the motor is rotated in a first direction (clockwise or counterclockwise) and the movable member slides or translates to the second position when the drive shaft is reversed and rotated in the opposite direction. Eccentric force causes the movable member 58 to move to the opposite end of the slot 68 when the motor is reversed. It will be appreciated that the movable member 58 will be located at the first position, as shown in FIG. 23, when the eccentric weight member 54 is rotated clockwise (based on the configuration shown in FIG. 23) and the movable member 58 will be located at the second position, as shown in FIG. 24, when the eccentric weight member 54 is rotated counterclockwise (based on the configuration shown in FIG. 24). Essentially, the opposite ends of slot 68 are stop members that stop the movable member 58 as it moves when the motor direction is reversed. In short, the direction of rotation of the motor drive shaft determines the amplitude of the reciprocating movement of the reciprocating shaft and, therefore, the massage attachment.

FIGS. 23 and 24 also show the axis of rotation A1 of the eccentric weight member 54 and the axis of shaft 72 A2. As can be seen in a comparison of FIG. 23 to FIG. 24, the distance between A1 and A2 is greater when the movable member 58 is in the second position than when the movable member 58 is in the first position. As a result, the reciprocating shaft 20 has a greater amplitude or stroke when the movable member 58 is in the second position than when the movable member 58 is in the first position. In an exemplary embodiment, the amplitude is 8 mm when the movable member is in the first position (A1 is 4 mm from A2) and 16 mm when the movable member is in the second position (A1 is 8 mm from A2). These numbers are only exemplary and the range can be wider or small than discussed above. In a preferred embodiment, slot 68 is angled such that the first position end is closer to the axis of rotation A1 than the second end.

In an exemplary use, the user of the device has the ability to choose the amplitude by pushing a button or otherwise activating a switch (e.g., one button for each amplitude or subsequent pushes of the same button).

The button or switch can be on the device or can be on a software application "app" executable on an electronic mobile device, such as a phone. After the button is pushed, the selection of the amplitude is processed in the PCB and is translated into a motor shaft rotation direction (e.g., counter-clockwise amplitude A, clockwise amplitude B). The motor then begins rotating the shaft and the eccentric weight the appropriate direction, thereby causing the movable member to move to the position to result in the correct amplitude.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

Embodiments are envisioned where any of the aspects, features, component or steps herein may be omitted and/or are option. Furthermore, where appropriate any of these optional aspects, features, component or steps discussed herein in relation to one aspect of the invention may be applied to another aspect of the invention.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges. It will be appreciated that any dimensions given herein are only exemplary and that none of the dimensions or descriptions are limiting on the present invention.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A percussive therapy device comprising:
   a housing;
   an electrical source;
   a motor positioned in the housing, wherein the motor comprises a motor shaft configured to rotate with the motor at a center of rotation;
   a switch for activating the motor;
   a push rod assembly operatively connected to the motor and configured to provide reciprocating motion in response to activation of the motor, wherein the reciprocating motion of the push rod assembly has a user-adjustable amplitude;
   a massage attachment secured to a distal end of the push rod assembly; and
   a variable amplitude assembly that includes an eccentric weight member received on the motor shaft of the motor,
   wherein a rotational axis of the motor and a rotational axis of the variable amplitude assembly are aligned with each other,
   wherein the distal end of the push rod assembly is configured to reciprocate within a first range,
   wherein the amplitude is user-adjustable such that the distal end is configured to reciprocate within a second range,
   wherein the second range is different than the first range,
   wherein the variable amplitude assembly includes a movable member that is movable with respect to the eccentric weight member between a first position and a second position,
   wherein the movable member includes an offset shaft extending therefrom,
   wherein the push rod assembly is operatively connected to the offset shaft,
   wherein the distal end of the push rod assembly reciprocates within the first range when the movable member is in the first position,
   wherein the distal end of the push rod assembly reciprocates within the second range when the movable member is in the second position,
   wherein a slot is defined in the eccentric weight member,
   wherein the movable member includes a main body portion with a slide member extending therefrom, and
   wherein the slide member is received in and movable within the slot.

2. The percussive therapy device of claim 1, further comprising an input that changes the amplitude from the first range to the second range.

3. The percussive therapy device of claim 1,
   wherein the motor is configured to rotate the eccentric weight member about a first axis in a first direction and an opposite second direction,
   wherein when the eccentric weight member is rotated in the first direction, the distal end of the push rod assembly reciprocates within the first range, and
   wherein when the eccentric weight member is rotated in the second direction, the distal end of the push rod assembly reciprocates within the second range.

4. The percussive therapy device of claim 3, wherein the movable member is movable from the first position to the second position when the rotation of the eccentric weight member is reversed from the first direction to the second direction.

5. The percussive therapy device of claim 1, wherein the variable amplitude assembly includes an interference member that is positioned in a channel defined in the eccentric weight member,
- wherein the interference member is movable between a deployed position and a rest position,
- wherein in one of the deployed position or the rest position, the interference member prevents the movable member from moving between the first position and the second position, and
- wherein in the other of the deployed position and the rest position, the interference member does not prevent the movable member from moving between the first position and the second position.

6. The percussive massage device of claim 5, wherein in the deployed position, the interference member prevents the movable member from moving between the first position and the second position,
- wherein in the rest position, the interference member does not prevent the movable member from moving between the first position and the second position, and
- wherein the interference member is biased to the rest position by a spring.

7. The percussive massage device of claim 6, wherein the interference member is movable from the rest position to the deployed position when the eccentric weight member rotates at a predetermined RPM.

8. The percussive massage device of claim 6, wherein the interference member includes a stop member,
- wherein the movable member includes a tooth, and
- wherein in the deployed position, the stop member blocks the tooth to prevent the movable member from moving between the first position and the second position.

9. The percussive massage device of claim 5, wherein the interference member is movable from the rest position to the deployed position by the activation of an electromagnet.

10. The percussive massage device of claim 9, wherein the interference member includes a stop member,
- wherein the movable member includes a tooth, and
- wherein in the rest position, the stop member blocks the tooth to prevent the movable member from moving between the first position and the second position.

11. A method of using a percussive therapy device that includes a housing, an electrical source, a motor comprising a motor shaft and positioned in the housing, a switch for activating the motor, a push rod assembly operatively connected to the motor and configured to provide reciprocating motion in response to activation of the motor, a massage attachment secured to a distal end of the push rod assembly, and a variable amplitude assembly that includes an eccentric weight member received on the motor shaft of the motor, the method comprising steps of:
- (a) activating the motor and massaging a body part with the massage attachment, wherein the distal end of the push rod assembly reciprocates within a first range;
- (b) adjusting an amplitude of the reciprocation; and
- (c) activating the motor and massaging the body part with the massage attachment,
- wherein the distal end of the push rod assembly reciprocates within a second range,
- wherein the second range is different than the first range, and
- wherein a rotational axis of the motor and a rotational axis of the variable amplitude assembly are aligned with each other,
- wherein the variable amplitude assembly includes a movable member that is movable with respect to the eccentric weight member between a first position and a second position,
- wherein the movable member includes an offset shaft extending therefrom,
- wherein the push rod assembly is operatively connected to the offset shaft,
- wherein the distal end of the push rod assembly reciprocates within the first range when the movable member is in the first position,
- wherein the distal end of the push rod assembly reciprocates within the second range when the movable member is in the second position,
- wherein a slot is defined in the eccentric weight member,
- wherein the movable member includes a main body portion with a slide member extending therefrom, and
- wherein the slide member is received in and movable within the slot.

12. The method of claim 11, further comprising a step of activating an input to adjust the amplitude.

13. The method of claim 11,
- wherein during step (a) the motor shaft is rotated in a first direction, and
- wherein during step (c) the motor shaft is rotated in a second direction.

14. The method of claim 11,
- wherein during step (a) the eccentric weight member is rotated in a first direction, and
- wherein during step (c) the eccentric weight member is rotated in a second direction.

\* \* \* \* \*

UNITED STATES PATENT AND TRADEMARK OFFICE
CERTIFICATE OF CORRECTION

PATENT NO. : 11,957,635 B2
APPLICATION NO. : 17/515158
DATED : April 16, 2024
INVENTOR(S) : Wersland et al.

It is certified that error appears in the above-identified patent and that said Letters Patent is hereby corrected as shown below:

In the Claims

In Column 15, Claim 6, Line 15, delete "massage" and insert -- therapy --, therefor.

In Column 15, Claim 7, Line 24, delete "massage" and insert -- therapy --, therefor.

In Column 15, Claim 8, Line 28, delete "massage" and insert -- therapy --, therefor.

In Column 15, Claim 9, Line 34, delete "massage" and insert -- therapy --, therefor.

In Column 15, Claim 10, Line 37, delete "massage" and insert -- therapy --, therefor.

Signed and Sealed this
Third Day of September, 2024

Katherine Kelly Vidal
*Director of the United States Patent and Trademark Office*